(12) United States Patent
Gitler et al.

(10) Patent No.: US 8,865,411 B2
(45) Date of Patent: Oct. 21, 2014

(54) METHODS OF IDENTIFYING MODULATORS OF TDP-43 MEDIATED CELLULAR TOXICITY

(75) Inventors: Aaron D. Gitler, Foster City, CA (US); Andrew Elden, Hialeah, FL (US)

(73) Assignees: National Institutes of Health (NIH), Washington, DC (US); U.S. Dept. of Health and Human Services (DHHS), Washington, DC (US); NIH Division of Extramural Inventions and Technology Resources (DEITR), Washington, DC (US)

( * ) Notice: Subject to any disclaimer, the term of this patent is extended or adjusted under 35 U.S.C. 154(b) by 0 days.

(21) Appl. No.: 13/260,492

(22) PCT Filed: Mar. 26, 2010

(86) PCT No.: PCT/US2010/028821
§ 371 (c)(1),
(2), (4) Date: May 1, 2012

(87) PCT Pub. No.: WO2010/111587
PCT Pub. Date: Sep. 30, 2010

(65) Prior Publication Data
US 2012/0237499 A1 Sep. 20, 2012

Related U.S. Application Data

(60) Provisional application No. 61/163,703, filed on Mar. 26, 2009.

(51) Int. Cl.
*C12Q 1/68* (2006.01)
*G01N 33/53* (2006.01)
*G01N 33/567* (2006.01)
*C07H 21/02* (2006.01)

(52) U.S. Cl.
USPC ..... 435/6.16; 536/24.5; 435/320.1; 435/69.1; 435/325; 435/7.1; 435/7.21; 435/7.31

(58) Field of Classification Search
None
See application file for complete search history.

(56) References Cited

U.S. PATENT DOCUMENTS

| 2006/0084071 | A1 | 4/2006 | Muchowski et al. |
| 2006/0147902 | A1 | 7/2006 | Lindquist et al. |
| 2011/0053857 | A1* | 3/2011 | Lindquist et al. ............ 514/17.7 |

FOREIGN PATENT DOCUMENTS

WO WO 2009/102995 * 8/2009

OTHER PUBLICATIONS

Ye (Retrovirology 2005, 2:63).*
Johnson et al (Proc. Nat. Acad. Sci. USA 105(17): 6439-6444, 2008).*
Tai, H.C., et al. "Ubiquitin, the proteasome and protein degradation in neuronal function and dysfunction." Nat Rev Neurosci. Nov. 2008;9(11):826-38.
Espeseth, A.S., et al. "A genome wide analysis of ubiquitin ligases in APP processing identifies a novel regulator of BACE1 mRNA levels." Mol Cell Neurosci. Nov. 2006;33(3):227-35. Epub Sep. 15, 2006.

* cited by examiner

*Primary Examiner* — Richard Schnizer
(74) *Attorney, Agent, or Firm* — Dann, Dorfman, Herrell & Skillman; Kathleen D. Rigaut; Robert C. Netter, Jr.

(57) ABSTRACT

Compositions and methods are disclosed for identifying agents useful for the treatment of proteinopathies.

9 Claims, 11 Drawing Sheets

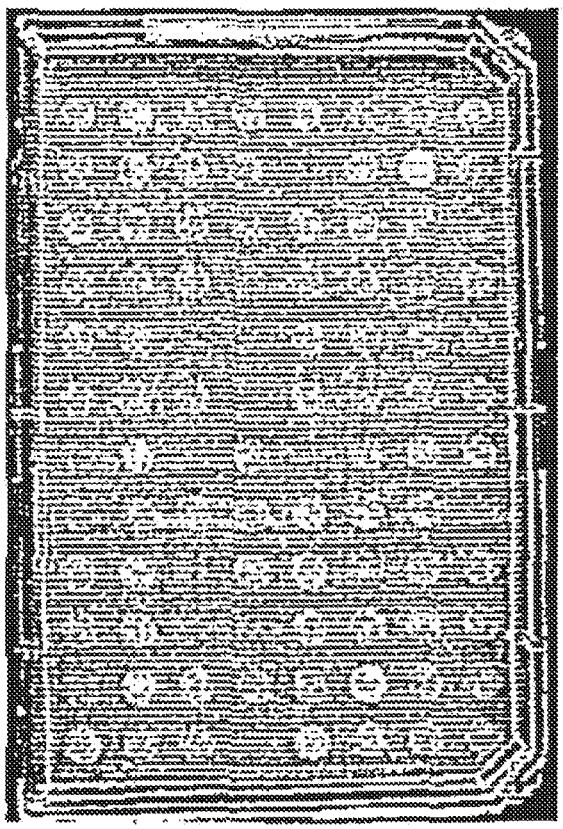
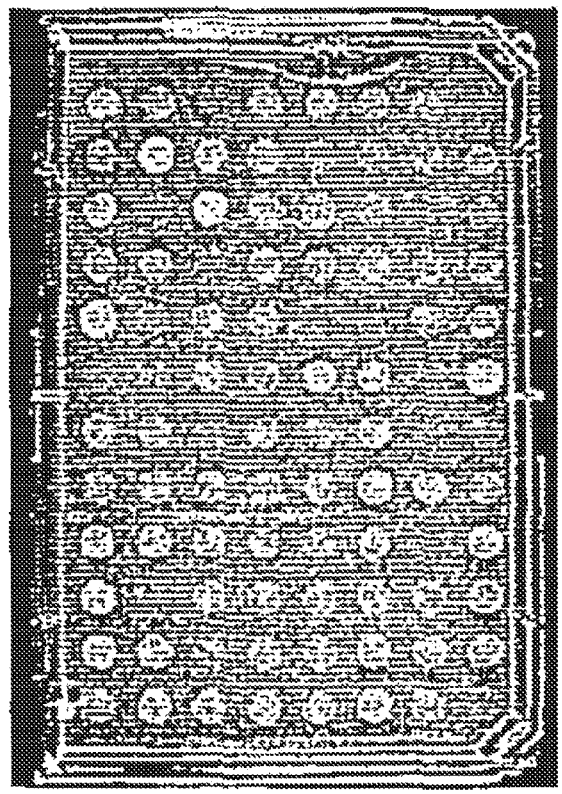
Figure 3

Figure 6A

```
  1 mseyirvted endepieips eddgtvllst vtaqfpgacg lryrnpvsqc mrgvrlvegi
 61 lhapdagwgn lvyvvnypkd nkrkmdetda ssavkvkrav qktsdlivlg lpwktteqdl
121 keyfstfgev lmvqvkkdlk tghskgfgfv rfteyetqvk vmsqrhmidg rwcdcklpns
181 kqsqdeplrs rkvfvgrcte dmtedelref fsqygdvmdv fipkpfrafa fvtfaddqia
241 qslcgedlii kgisvhisna epkhnsnrql ersgrfggnp ggfgnqggfg nsrgggaglg
301 nnqgsnmggg mnfgafsinp ammaaaqaal qsswgmmgml asqqnqsgps gnnqnqgnmq
361 repnqafgsg nnsysgsnsg aaigwgsasn agsgsgfngg fgssmdskss gwgm
```

Figure 6B

```
   1 ggtgggcggg gggaggaggc ggccctagcg ccattttgtg ggagcgaagc ggtggctggg
  61 ctgcgcttgg gtccgtcgct gcttcggtgt ccctgtcggg cttcccagca gcggcctagc
 121 gggaaaagta aaagatgtct gaatatattc gggtaaccga agatgagaac gatgagccca
 181 ttgaaatacc atcggaagac gatgggacgg tgctgctctc cacggttaca gcccagtttc
 241 caggggcgtg tggcttcgc tacaggaatc cagtgtctca gtgtatgaga ggtgtccggc
 301 tggtagaagg aattctgcat gccccagatg ctggctgggg aaatctggtg tatgttgtca
 361 actatccaaa agataacaaa agaaaatgg atgagacaga tgcttcatca gcagtgaaag
 421 tgaaaagagc agtccagaaa acatccgatt taatagtgtt gggtctccca tggaaaacaa
 481 ccgaacagga cctgaaagag tattttagta cctttggaga agttcttatg gtgcaggtca
 541 agaaagatct taagactggt cattcaaagg ggtttggctt tgttcgtttt acggaatatg
 601 aaacacaagt gaaagtaatg tcacagcgac atatgataga tggacgatgg tgtgactgca
 661 aacttcctaa ttctaagcaa agccaagatg agcctttgag aagcagaaaa gtgtttgtgg
 721 ggcgctgtac agaggacatg actgaggatg agctgcggga gttcttctct cagtacgggg
 781 atgtgatgga tgtcttcatc cccaagccat tcagggcctt tgcctttgtt acatttgcag
 841 atgatcagat tgcgcagtct ctttgtggag aggacttgat cattaaagga atcagcgttc
 901 atatatccaa tgccgaacct aagcacaata gcaatagaca gttagaaaga agtggaagat
 961 ttggtggtaa tccaggtggc tttgggaatc agggtggatt tggtaatagc agaggggtg
1021 gagctggttt gggaaacaat caaggtagta atatgggtgg tgggatgaac tttggtgcgt
1081 tcagcattaa tccagccatg atggctgccg cccaggcagc actacagagc agttggggta
1141 tgatgggcat gttagccagc cagcagaacc agtcaggccc atcgggtaat aaccaaaacc
1201 aaggcaacat gcagagggag ccaaaccagg ccttcggttc tggaaataac tcttatagtg
1261 gctctaattc tggtgcagca attggttggg gatcagcatc caatgcaggg tcgggcagtg
1321 gtttttaatgg aggctttggc tcaagcatgg attctaagtc ttctggctgg ggaatgtaga
1381 cagtggggtt gtggttggtt ggtatagaat ggtgggaatt caaattttt caaactcatg
1441 gtaagtatat tgtaaaatac atatgtacta agaattttca aaattggttt gttcagtgtg
1501 gagtatattc agcagtattt ttgacatttt tctttagaaa aaggaagagc taaaggaatt
1561 ttataagttt tgttacatga aaggttgaaa tattgagtgg ttgaaagtga actgctgttt
1621 gcctgattgg taaaccaaca cactacaatt gatatcaaaa ggtttctcct gtaatatttt
1681 atccctggac ttgtcaagtg aattctttgc atgttcaaaa cggaaaccat tgattagaac
1741 tacattcttt accccttgtt ttaatttgaa ccccaccata tggatttttt tccttaagaa
1801 aatctccttt taggagatca tggtgtcaca gtgtttggtt cttttgtttt gttttttaac
1861 acttgtctcc cctcatacac aaaagtacaa tatgaagcct tcatttaatc tctgcagttc
1921 atctcatttc aaatgtttat ggaagaagca cttcattgaa agtagtgctg taaatattct
1981 gccataggaa tactgtctac atgctttctc attcaagaat tcgtcatcac gcatcacagg
2041 ccgcgtcttt gacggtgggt gtcccatttt tatccgctac tcttatttc atggagtcgt
2101 atcaacgcta tgaacgcaag gctgtgatat ggaaccagaa ggctgtctga acttttgaaa
2161 ccttgtgtgg gattgatggt ggtgccgagg catgaaaggc tagtatgagc gagaaaagga
2221 gagagcgcgt gcagagactt ggtggtgcat aatggatatt ttttaacttg gcgagatgtg
2281 tctctcaatc ctgtggcttt ggtgagagag tgtgcagaga gcaatgatag caaataatgt
2341 acgaatgttt tttgcattca aaggacatcc acatctgttg gaagactttt aagtgagttt
2401 ttgttcttag ataacccaca ttagatgaat gtgttaagtg aaatgatact tgtactcccc
2461 ctaccccttt gtcaactgct gtgaatgctg tatggtgtgt gttctcttct gttactgata
2521 tgtaagtgtg gcaatgtgaa ctgaagctga tgggctgaga acatggactg agcttgtggt
2581 gtgctttgca ggaggacttg aagcagagtt caccagtgag ctcaggtgtc tcaaagaagg
2641 gtggaagttc taatgtctgt tagctaccca taagaatgct gtttgctgca gttctgtgtc
2701 ctgtgcttgg atgcttttta taagagttgt cattgttgga aattcttaaa taaaactgat
2761 ttaaataata tgtgtctttg ttttcagcc ctgaatgcaa agaattcata gcagttaatt
2821 ccccttttt gacccttttg agatggaact ttcataaagt ttcttggcag tagtttattt
2881 tgcttcaaat aaacttattt gaaaagttgt ctcaagtcaa atggattcat cacctgtcat
2941 gcattgacac ctgatacca gacttaattg gtatttgttc ttgcattggc caaagtgaaa
3001 attttttttt ttcttttgaa atctagtttt gaataagtct gggtgaccgc acctaaaatg
3061 gtaagcagta ccctccggct ttttcttagt gcctctgtgc atttgggtga tgttctattt
```

Figure 6B continued

```
3121 acatggcctg tgtaaatctc cattgggaag tcatgccttc taaaaagatt cttatttggg
3181 ggagtgggca aaatgttgat tattttctaa tgctttgtag caaagcatat caattgaaaa
3241 gggaatatca gcaccttcct agtttgggat ttgaaaagtg gaattaattg cagtagggat
3301 aaagtagaag aaaccacaaa ttatcttgtg cctgaaatcc attaagaggc ctgatagctt
3361 taagaattag ggtgggttgt ctgtctggaa gtgttaagtg gaatgggctt tgtcctccag
3421 gaggtggggg aatgtggtaa cattgaatac agttgaataa aatcgcttac aaaactcaca
3481 ctctcacaat gcattgttaa gtatgtaaaa gcaataacat tgattctctg ttgtactttt
3541 ttgtaactaa ttctgtgaga gttgagctca ttttctagtt ggaagaatgt gatatttgtt
3601 gtgttggtag tttacctaat gcccttacct aattagatta tgataaatag gtttgtcatt
3661 ttgcaagtta cataaacatt tatcaatgaa gtcatccttt agacttgtaa tcgccacatt
3721 gtttcattat tcagtttcct ctgtaaaggg atcttgagtt gttttaattt ttttttttctg
3781 catctgaatc tgcatgattt ccaaaccctg taccatctga attttgcatt ttagcacttg
3841 cactattact cagcagcagt aacatggtaa cacttaaaat ggtactcggg gacctccaaa
3901 gactaaactg acaagccttc aaggagccca ggggtaagtt aacttgtcaa cggcatggtt
3961 taatcccttc tttacacttg tgtaaatttc agttactggt catagaaggc tttcaatgtt
4021 gagtggcctt ttattaacat gtttatggta ctgcatagat acgggtattt attttaccct
4081 aagaagattt tgaagtttaa aagtacttaa actatttggc aaagatttgt ttttaaaaat
4141 ctatttggtc aatctaaatg cattcattct aaaaaatttt ttgaaccaga taaataaaat
4201 ttttttttga caccacaaaa aaaaaaaaaa aaaaa
```

METHODS OF IDENTIFYING MODULATORS OF TDP-43 MEDIATED CELLULAR TOXICITY

This application is a §371 application of PCT/US2010/028821 filed Mar. 26, 2010, which claims priority to U.S. Provisional Application No. 61/163,703 filed Mar. 26, 2009, the entire contents of each being incorporated herein by reference as though set forth in full.

Pursuant to 35 U.S.C. §202(c) it is acknowledged that the U.S. Government has certain rights in the invention described, which was made in part with funds from the National Institutes of Health, Grant Number 1DP20D004417-01.

FIELD OF THE INVENTION

The present invention relates to the fields of medicine, protein folding and neurobiology. More specifically, the invention provides a series of genetic modulators of TDP-43 activity, which in the presence of full length or functional TDP-43 C-terminal variants augment or suppress TDP-43 mediated toxicity and aberrant protein aggregation. These molecules have utility in screening assays to identify agents useful for the treatment of disorders associated with aberrant protein aggregation, particularly neurological diseases, such as amyotrophic lateral sclerosis (ALS), fronto-temporal lobar degeneration (FTLD), Parkinson's disease, Huntington's disease and Alzheimer's disease (AD).

BACKGROUND OF THE INVENTION

Several publications and patent documents are cited throughout the specification in order to describe the state of the art to which this invention pertains. Each of these citations is incorporated by reference herein as though set forth in full.

The United States and other countries around the world are experiencing a demographic sea change owing to the rapidly growing elderly and 'Baby Boomer' populations (Trojanowski, (2008) Neurosignals 16: 5-10). Our astonishing biomedical advances in the last half-century have greatly increased our life expectancy. But as a consequence of living longer, our population now faces an up tick in the incidence of neurodegenerative diseases. These truly disastrous disorders include Alzheimer's, Huntington's, Parkinson's, amyotrophic lateral sclerosis (ALS) and the frontal temporal dementias (Forman et al. (2004) Nat. Med. 10:1055-1063). Interestingly, though disparate in their pathophysiology, many of these diseases share a common molecular theme manifesting in the accumulation of insoluble protein aggregates in the brain and nervous system. Deciphering the mechanisms causing these proteins to misfold and aggregate and identifying the genes and cellular pathways affected by misfolded human disease proteins will aid the development of new therapeutic approaches, which we are in dire need of.

The protein TDP-43 was recently identified as the major disease protein in pathological inclusions in both ALS and frontal temporal lobar degeneration with ubiquitin-positive inclusions (FTLD-U) (Neumann et al. (2006) Science 314: 130-133). Moreover, mutations in the TDP-43 gene have now been identified in sporadic and familial ALS patients (Gitcho et al., (2008) Ann Neurol. 63:535-8; Kabashi et al., (2008) Nat Genet. 40: 572-574; Sreedharan et al., (2008) Science 319: 1668-1672; Van Deerlin et al., (2008) Lancet Neurol. 7: 409-416); Yokoseki et al., (2008) Ann Neurol. 63: 538-542. Pathology and genetics both converge on TDP-43 as being central to the pathogenesis of these diseases. The study of tau, α-synuclein, and amyloid beta in neurodegenerative disorders has revolutionized our understanding of their respective disease mechanisms. A similar intense effort to understand TDP-43 biology and its role in pathology will be beneficial to the development of therapies to treat proteinopathies such as ALS and FTLD-U.

SUMMARY OF THE INVENTION

In accordance with the present invention, compositions and methods are provided for the treatment and prevention of proteinopathy disorders. The present inventor has identified a variety of TDP-43 toxicity modulators via overexpression assays and deletion assays. The modulators act to suppress or enhance TDP-43 mediated toxicity and/or aberrant protein aggregation in TDP-43 expressing cells. Accordingly, the molecules identified in Tables 1 and 2 provide new beneficial therapeutic targets for the development of agents useful for the treatment of disorders associated with aberrant protein folding and deposition.

An exemplary method for treating or inhibiting development of a proteinopathy in a subject in need thereof comprises administering an effective amount of a pharmaceutical activity of at least one gene selected from the group consisting of MEC1, SAK1, YCK2, VHS1, KIN3, PCL6, UBP7, KEM1, PBP1, MSN5, SRO9, SLF1, HRP1, PBP2, SFG1, MSA1, YHR131C, SOL1, CDC6, RGA2, SLG1, ROM2, KEL1, TSC11, DIP5, PIB2, MTH1, SET3, DBR1, CCE1, SIW14, YDR067C, DOM34, MGD1, RPL16 and human homologs thereof, said inhibition being effective to reduce cytotoxicity and/or aberrant protein aggregation in said subject. Proteinopathy disorders to be treated include, without limitation, amyotrophic lateral sclerosis (ALS), fronto-temporaral dementia (FTD), fronto-temporal lobar degeneration (FTLD), Parkinson's disease (PD), Huntington's disease (HD) and Alzheimer's disease (AD). In a preferred embodiment, the agent inhibits expression of DBR-1.

Also provided is a method of inhibiting TDP-43 mediated cellular toxicity. In this embodiment, a cell expressing a toxicity inducing amount TDP-43 or a functional C-terminal variant thereof is contacted with an effective amount of an agent that inhibits expression or activity of at least one yeast gene selected from the group consisting of MEC1, SAK1, YCK2, VHS1, KIN3, PCL6, UBP7, KEM1, PBP1, MSN5, SRO9, SLF1, HRP1, PBP2, SFG1, MSA1, YHR131C, SOL1, CDC6, RGA2, SLG1, ROM2, KEL1, TSC11, DIP5, PIB2, MTH1, SET3, DBR1, CCE1, SIW14, YDR067C, DOM34, MGD1, RPL16, and human homologs thereof, said inhibition being associated with a reduction in TDP-mediated cellular toxicity and protein aggregation. In a preferred embodiment, the agent inhibits expression of DBR1.

Yet another embodiment of the invention is a screening assay for identifying agents which inhibit TDP-43 mediated cellular toxicity, comprising providing a cell which expresses wild type TDP-43 or a C-terminal functional variant of thereof containing amino acids 188-414, said expression being associated with increased protein aggregation and cellular toxicity. The cells are contacted with an effective amount of an agent which inhibits expression or activity of at least one gene selected from the group consisting of MEC1, SAK1, YCK2, VHS1, KIN3, PCL6, UBP7, KEM1, PBP1, MSN5, SRO9, SLF1, HRP1, PBP2, SFG1, MSA1, YHR131C, SOL1, CDC6, RGA2, SLG1, ROM2, KEL1, TSC11, DIP5, PIB2, MTH1, SET3, DBR1, CCE1, SIW14, YDR067C, DOM34, MGD1, RPL16 and human homologs thereof; and protein aggregation and cellular toxicity are measured in the presence of said agent relative to a non-treated control, wherein a decrease in protein aggregation and cellular toxicity identifies an agent which reduces TDP-43 mediated cellular toxicity. Alternatively, the effect of the agent on cellular viability may be determined. Pharmaceutical compositions comprising the agents so identified in a biologically acceptable carrier also form an aspect of the invention.

Also disclosed is a method for treating or inhibiting development of a proteinopathy in a subject in need thereof. An exemplary method entails administering an effective amount of a pharmaceutical composition comprising a therapeutic amount of an agent which increases expression or activity of at least one yeast gene selected from the group consisting of HSP104, YKL171W, FMP48, RIM15, BFR1, VTS1, TIS11, CYC8, RDR1, ISC2, ADY3, XRS2, PGM1, TIF4631, MRPL39, FLD1, MSN2, PBL16B, NHX1 and human homologs thereof, said increase being effective to reduce cytotoxicity and/or aberrant protein aggregation in said subject.

In a further aspect, a method of inhibiting TDP-43 mediated cellular toxicity is provided. An exemplary method comprises contacting a cell expressing a toxicity inducing amount TDP-43 or a functional C-terminal variant thereof with an effective amount of an agent that increases expression or activity of at least one gene selected from the group consisting of HSP104, YKL171W, FMP48, RIM15, BFR1, VTS1, TIS11, CYC8, RDR1, ISC2, ADY3, XRS2, PGM1, TIF4631, MRPL39, FLD1, MSN2, PBL16B, NHX1 and human homologs thereof, said increase being associated with a reduction in cellular toxicity and protein aggregation.

An alternative method for identifying agents which inhibit TDP-43 mediated cellular toxicity is also provided. This method comprises providing a cell which expresses wild type TDP-43 or a C-terminal functional variant of thereof containing amino acids 188-414, said expression being associated with increased protein aggregation and cellular toxicity; contacting said cell with an effective amount of an agent which increases expression or activity of at least one gene selected from the group consisting of HSP104, YKL171W, FMP48, RIM15, BFR1, VTS1, TIS11, CYC8, RDR1, ISC2, ADY3, XRS2, PGM1, TIF4631, MRPL39, FLD1, MSN2, PBL16B, NHX1 and human homologs thereof; and measuring protein aggregation and cellular toxicity in the presence of said agent relative to a non-treated control, wherein a decrease in protein aggregation and cellular toxicity identifies an agent which reduces TDP-43 mediated cellular toxicity. Alternatively, the effect of the agent on cellular viability may be determined. Pharmaceutical compositions comprising agents so identified (e.g., siRNA which specifically down modulate DBR1 expression levels) in a biologically acceptable carrier also form an embodiment of the invention.

BRIEF DESCRIPTION OF THE DRAWINGS

FIG. 1A: A diagram illustrating the domain structure of TDP-43 along with various truncation constructs used in this study (a-1). FIG. 1B: Structure/function analysis testing the effects of truncations on TDP-43-GFP localization by fluorescence microscopy and toxicity by spotting assays. FIG. 1C: The C-terminal region is required for aggregation and toxicity compare constructs a and d), but by itself is not sufficient (construct j). A construct harboring the C-terminus along with RRM2 recapitulates the complete aggregation and toxicity of full-length TDP-43 (construct g). RRM, RNA recognition motif; C-term, carboxy terminus; NLS, nuclear localization signal.

FIG. 3: Examples of plates from pilot TDP-43 modulator screen. We identified yeast genes that reproducibly suppress or enhance TDP-43 toxicity when overexpressed.

FIG. 6: Sequences encoding human TDP-43. FIG. 6A: Amino acid sequence of TDP-43 (SEQ ID NO: 1). C-terminal variant sequence is underlined. FIG. 6B: Nucleic acid encoding TDP-43 protein (SEQ ID NO: 2).

DETAILED DESCRIPTION OF THE INVENTION

Figure 1:
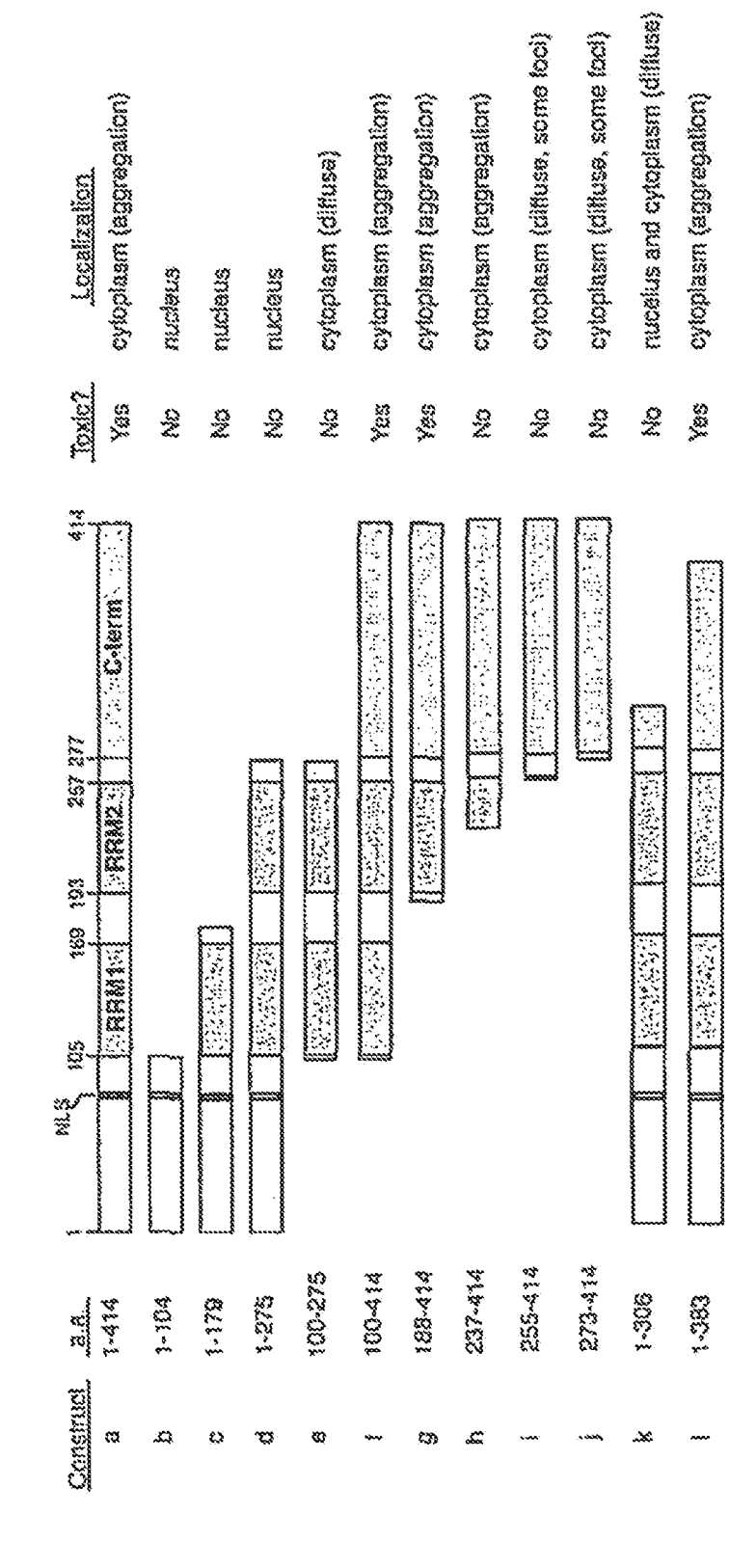
FIG. 1: Identification of the molecular determinants of TDP-43 aggregation and toxicity.
Figure 1:
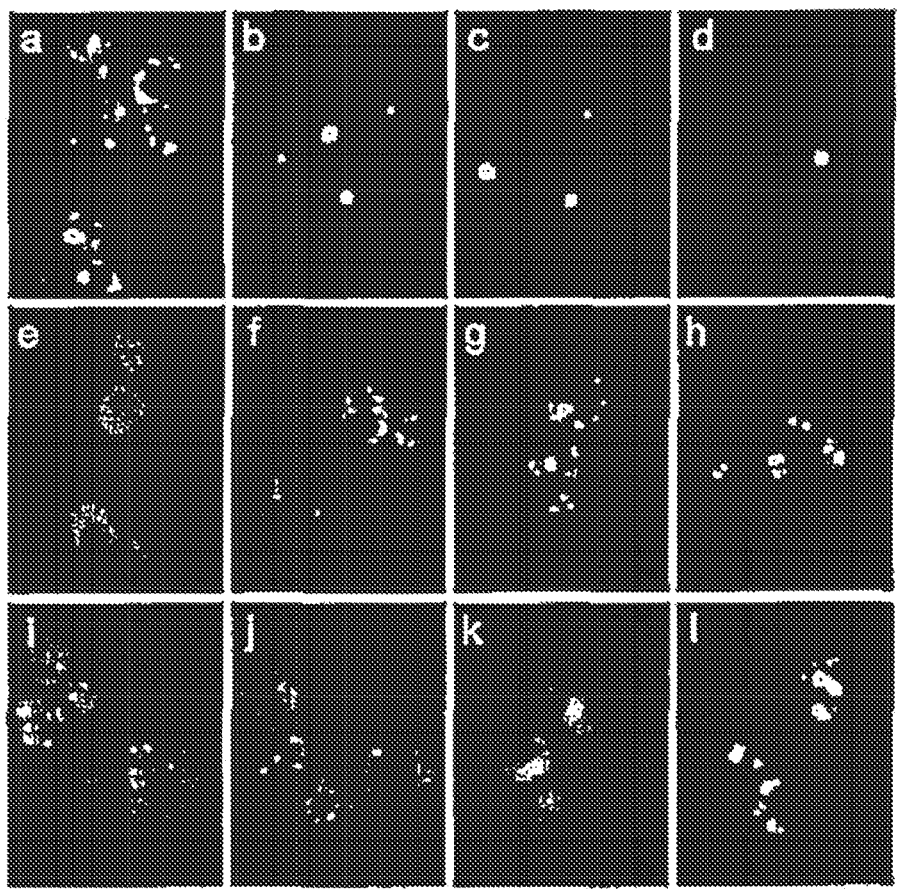
Figure 1:
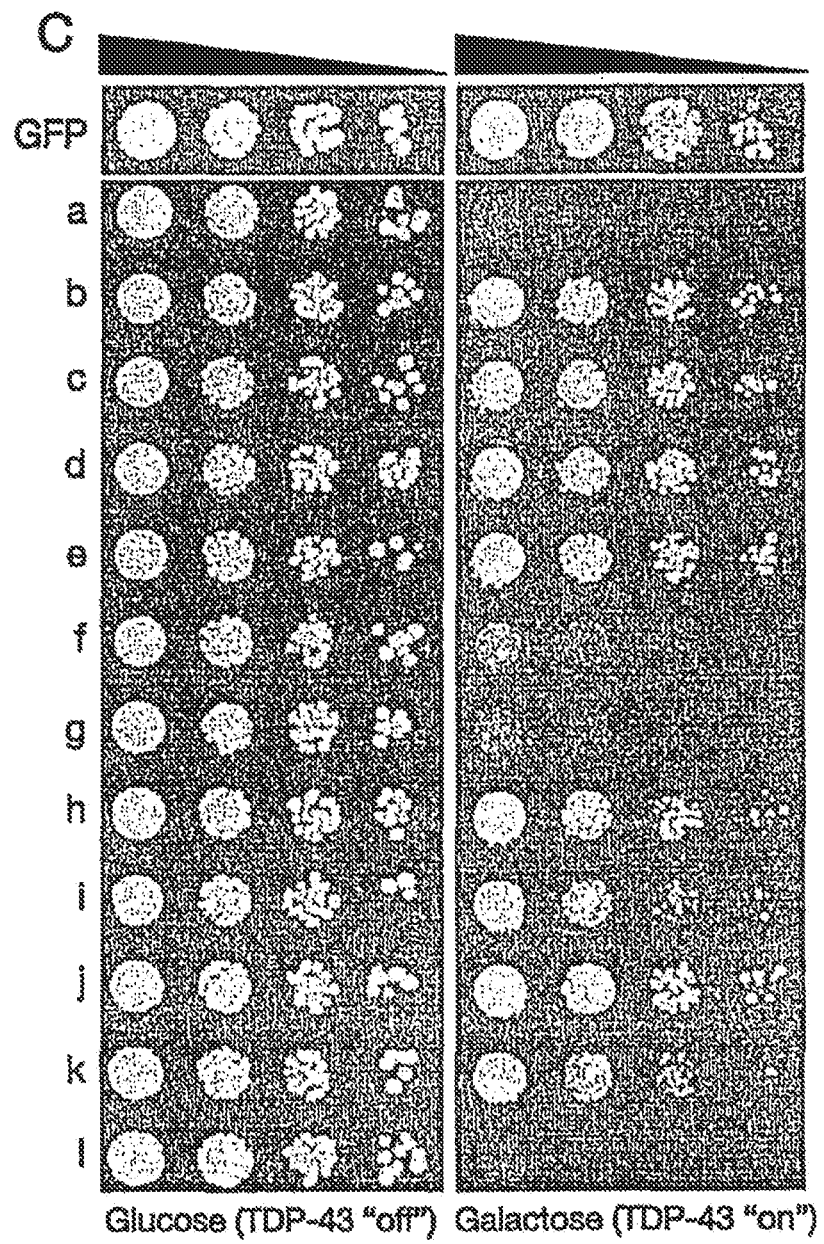

TDP-43 is a highly conserved, ubiquitously expressed protein, initially identified by virtue of its ability to bind the HIV-1 TAR DNA element and act as a transcriptional repressor (Ou et al. 1995). In addition to a glycine-rich C-terminal region, TDP-43 contains two RNA recognition motifs (RRMI and RRM2) and is able to bind UG-repeats in RNA (Buratti et al. (2001) J. Biol. Chem. 276: 36337-43; Strong et al. (2007) Mol Cell Neurosci 35:320-327). Some reports suggest TDP-43 might play a role in regulating splicing (Ayala et al. (2006) FEBS Lett 580:1339-1344), while others propose it can act as a kind of bridge for nuclear bodies via an interaction with the survival motor neuron (SMN) protein (Wang et al. (2002) Proc Natl Acad Sci 99: 13583-8). Mouse knockouts of TDP-43 have not been reported, but knock-down of TDP-43 function by siRNA in human cell culture results in defects in nuclear shape, cell cycle abnormalities and apoptosis, owing to a failure to effectively repress transcription of cyclin-dependent kinase 6 (Ayala et al. (2008) Proc Natl Acad Sci 105: 3785-3789).

The recent discovery of pathological TDP-43 in both amyotrophic lateral sclerosis and frontotemporal lobar degeneration with ubiquitinated inclusions confirms that these are closely related conditions within a new biochemical class of neurodegenerative disease, the TDP-43 proteinopathies. In efforts to understand how TDP-43 causes disease (loss- or gain-of-function mechanism), we have generated in vitro and in vivo TDP-43 proteinopathy models to explore TDP-43 function and our results demonstrate: 1) an important role for the RNA recognition motif and carboxy-terminal region of TDP-43 in mediating aggregation and cellular toxicity, and 2) a variety of proteins referred to herein as "TDP-43 activity modulators", including multiple RNA binding proteins, are potent regulators of TDP-43 associated toxicity and aberrant protein aggregation.

These TDP-43 activity modulators which suppress or enhance TDP-43 mediated cellular toxicity and protein aggregation can be used to advantage in screening assays to identify agents which modulate protein folding and deposition. Compounds that modulate expression of these genes or activity of the encoded proteins can be used to inhibit TDP-43 mediated toxicity and used to treat or prevent proteinopathy disorders such as amyotrophic lateral sclerosis (ALS), frontotemporal lobar degeneration (FTLD), fronto-temporal dementia (FTD) and Alzheimer's disease (AD).

For those genes that were found to suppress toxicity when overexpressed in yeast, it is expected that enhancing expression of the genes and/or activity of proteins encoded by the genes will result in a suppression of toxicity in TDP-43 expressing cells. Such genes include, FMP48, VTS1, XRS2, HSP104, TIS11, BFR1, ICS2, YKL171W, PGM1, ADY3, RIM15, CYC8 and RDR1. Conversely, for those genes that were found to enhance toxicity when overexpressed in yeast, it is expected that inhibiting expression of the genes and/or the activity of proteins encoded by the genes will result in a suppression of toxicity in TDP-43 expressing cells. Such genes include, PCL6, SAK1, YCK2, MEC1, UBP7, RGA2, KEL1, DIP5, ROM2, VHS1, YHR131C, SLF1, HRP1, PBP1, KEM1, MSN5, SRO9, SFG1, MSA1, PIB2, SLG1, MTH1, CDC6, TSC11, SOL1, KIN3, and PBP2. Novel targets were also identified that suppress toxicity when deleted in yeast. Thus, inhibition of these molecules for inhibiting TDP-43 mediated toxicity is desirable. These genes include SET3, DBR1, CCE1, SIW14, YDR067C, DOB34, MGD1 and RPL16. Several approaches for enhancing or inhibiting target gene expression are provided below. Also identified in the deletion screen were genes which enhanced TDP-43 toxicity. Thus, in certain instances increasing expression levels of these genes should reduce or inhibit TDP-43 mediated toxicity. These genes and encoded proteins include, for example, TIF4361, MRPL39, FLD1, MSN2, PBL16B and NHX1.

Mechanisms by which TDP-43 protein induces toxicity in the yeast model system described herein should recapitulate the mechanisms by which TDP-43 induces toxicity in human cells. Many of the yeast genes identified as modulating TDP-43 mediated toxicity in yeast cells have orthologous or highly related genes in humans (See Table 1 and Table 2). As a result, human counterparts of the identified yeast genes are expected to be useful targets for modulating TDP-43 mediated toxicity in human cells.

Tables 1 and 2 list GenBank™ Accession Numbers corresponding to the nucleotide and protein sequences for human homologs of the yeast genes identified herein. As detailed hereinbelow, these nucleotide and protein sequences can be used to generate compounds (including but not limited to nucleic acids, peptides, antibodies, small molecules) that modulate expression of genes or activity of encoded gene products. The genes identified herein as modulators of TDP-43 mediated toxicity are referred to in subsequent sections (e.g., regarding screening assays) as "target genes" and the encoded proteins are referred to as "target proteins.

The data presented herein reveal that the TDP-43 activity modulators or "target proteins" are active in a variety of essential biochemical processes and pathways. These include RNA metabolism including binding and stability, control of the cell cycle, control of stress responses and transcriptional regulation. These putative functions are listed in the candidate therapeutics on these particular biochemical pathways in the context of the TDP-43 expressing yeast model described.

DEFINITIONS

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, Aisolated@ and Abiologically pure@ do not necessarily reflect the extent to which the compound has been purified. An isolated compound of the present invention can be obtained from its natural source, can be produced using laboratory synthetic techniques or can be produce; d by any such chemical synthetic route. "A TDP-43 protein" used in the compositions and methods described herein may be a naturally occurring wild-type protein, a mutated TDP-43 protein associated with a proteinopathy, or a C-terminal variant (See FIG. 1). Human TDP-43 is 414 amino acids in length (GenBank Reference:NP_031401; SEQ ID NO: 1). Particularly preferred is the C-terminal variant encoded by construct g, which contains amino acids 188-414 of SEQ ID NO: 1. The nucleic acid encoding Human TDP-43 is provided at GenBank reference: NP_007375; SEQ ID NO: 2. See FIGS. 1 and 6.

A "TDP-43 activity modulator" refers to a protein which enhances or inhibits TDP-43 associated toxicity and/or protein aggregation. Exemplary proteins include, without limitation, those proteins provided in Tables 1 and 2. The nucleic acid molecules encoding the proteins listed in Tables 1 and 2, may also be referred to as genetic modulators of TDP-43 activity. Modulation of the expression levels of these proteins may directly impact cellular viability in TDP-43 expressing cells.

A "proteinopathy" is a disease which is characterized by accumulation of toxic insoluble protein aggregates in cells. Exemplary disorders, include, without limitation, ALS, FTD, FTLD-U, Alzheimer's disease, Huntington's disease, Parkinson's disease, and other motor neuron diseases.

Agents which modulate "TDP-43 mediated cellular toxicity" are those agents which affect at least one of cellular viability, morphology, aberrant protein aggregation, and replication in the presence of TDP-43 or functional variants thereof.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence. With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and Atransduction@ refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA.

In one embodiment, the promoter element of the present invention precedes the 5' end of the TDP-43 or genetic modifier encoding nucleic acid molecule such that the latter is transcribed into mRNA. Host cell machinery then translates mRNA into a polypeptide. As mentioned hereinbelow, a variety of transgenic organisms are contemplated for use in the screening assays of the invention.

Those skilled in the art will recognize that a nucleic acid vector can contain nucleic acid elements other than the promoter element and the genetic modulator encoding nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, zebrafish, worm, insect and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene@ refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism" or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

Methods of Using TDP-43 Activity Modulators in the Presence of TDP-43 or Functional Variants Thereof for Development of Therapeutic Agents The methods described herein include methods (also referred to herein as "screening assays") for identifying compounds that modulate (i.e., increase or decrease) expression or activity of selected target genes or their protein products. Such compounds include, e.g., polypeptides, peptides, antibodies, peptidomimetics, peptoids, small inorganic molecules, small non-nucleic acid organic molecules, nucleic acids (e.g., anti-sense nucleic acids, siRNA, oligonucleotides, synthetic oligonucleotides), carbohydrates, or other agents that bind to the target proteins, have a stimulatory or inhibitory effect on, for example, expression of a target gene or activity of a target protein. Compounds thus identified can be used to modulate the expression or activity of target genes or target proteins in a therapeutic protocol.

In general, screening assays involve assaying the effect of a test agent on expression or activity of a target nucleic acid or target protein in a test sample (i.e., a sample containing the target nucleic acid or target protein). Expression or activity in the presence of the test compound or agent can be compared to expression or activity in a control sample (i.e., a sample containing the target protein that is incubated under the same conditions, but without the test compound). A change in the expression or activity of the target nucleic acid or target protein in the test sample compared to the control indicates that the test agent or compound modulates expression or activity of the target nucleic acid or target protein and is a candidate agent.

Compounds can be tested for their ability to modulate one or more activities mediated by a target protein described herein. For example, compounds that modulate expression of a gene or activity of a protein listed in Table 1 or Table 2 can be tested for their ability to modulate toxicity in cells expressing TDP-43 or C-terminal variants thereof. Methods of assaying a compound for such activities are known in the art. In some cases, a compound is tested for it's ability to directly affect target gene expression or binding to a target protein (e.g., by decreasing the amount of target RNA in a cell or decreasing the amount of target protein in a cell) and tested for its ability to modulate a metabolic effect associated with the target protein.

In one embodiment, assays are provided for screening candidate or test molecules that are substrates of a target protein or a biologically active portion thereof in a cell. In another embodiment, the assays are for screening candidate or test compounds that bind to a target protein or modulate the activity of a target protein or a biologically active portion thereof. Such compounds include those that disrupt the interaction between a target protein and its ligand. The test compounds used in the methods can be obtained using any of the numerous approaches in the art including combinatorial library methods, including: biological libraries; peptoid libraries (libraries of molecules having the functionalities of peptides, but with a novel, non-peptide backbone which are resistant to enzymatic degradation but which nevertheless remain bioactive; e.g., Zuckermann et al. (1994) J. Med. Chem. 37:2678); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the literature, for example in: DeWitt et al., Proc. Natl. Acad. Sci. USA, 90:6909, 1993; Erb et al., Proc. Natl. Acad. Sci. USA, 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl., 33:2061, 1994; and Gallop et al., J. Med. Chem., 37: 1233, 1994. Libraries of compounds may be presented in solution (e.g., Houghten, Bio/Techniques, 13:412421, 1992), or on beads (Lam, Nature, 354:82-84, 1991), chips (Fodor, Nature 364: 555-556, 1993), bacteria (U.S. Pat. No. 5,223,409), spores (U.S. Pat. Nos. 5,571,698; 5,403,484; and 5,223,409), plasmids (Cull et al., Proc. Natl. Acad. Sci. USA, 89:1865-1869, 1992) or phage (Scott and Smith, Science, 249:386-390, 1990; Devlin, Science, 249:404-406, 1990; Cwirla et al., Proc. Natl. Acad. Sci. USA, 87:6378-6382, 1990; and Felici, J. Mol. Biol., 222:301-310, 1991).

In one embodiment, a cell-based assay is employed in which a cell that expresses a target protein or biologically active portion thereof is contacted with a test compound. The ability of the test compound to modulate expression or activity of the target protein is then determined. The cell, for example, can be a yeast cell or a cell of mammalian origin, e.g., rat, mouse, zebrafish, *drosophila, C. elegans* or human.

The ability of the test compound to bind to a target protein or modulate target protein binding to a compound, e.g., a target protein substrate, can also be evaluated. This can be accomplished, for example, by coupling the compound, e.g., the substrate, with a radioisotope or enzymatic label such that binding of the compound, e.g., the substrate, to the target protein can be determined by detecting the labeled compound, e.g., substrate, in a complex. Alternatively, the target protein can be coupled with a radioisotope or enzymatic label to monitor the ability of a test compound to modulate target protein binding to a target protein substrate in a complex. For example, compounds (e.g., target protein substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a target protein substrate) to interact with target protein with or without the labeling of any of the interactants can be evaluated. For example, a microphysiometer can be used to detect the interaction of a compound with a target protein without the labeling of either the compound or the target protein (McConnell et al., Science 257:1906-1912, 1992). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between a compound and a target protein.

In yet another embodiment, a cell-free assay is provided in which a target protein or biologically active portion thereof is contacted with a test compound and the ability of the test compound to bind to the target protein or biologically active portion thereof is evaluated. In general, biologically active portions of target proteins to be used in assays described herein include fragments that participate in interactions with other molecules, e.g., fragments with high surface probability scores. Cell-free assays involve preparing a reaction mixture of the target protein and the test compound under conditions and for a time sufficient to allow the two components to interact and bind, thus forming a complex that can be removed and/or detected.

The interaction between two molecules can also be detected using fluorescence energy transfer (FET) (see, for example, Lakowicz et al., U.S. Pat. No. 5,631,169; Stavrianopoulos et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, the "donor" protein molecule may use the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

In another embodiment, the ability of a target protein to bind to a target molecule can be determined using real-time Biomolecular Interaction Analysis (BIA) (e.g., Sjolander et al., Anal. Chem., 63:2338-2345, 1991, and Szabo et al., Curr. Opin. Struct. Biol., 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In various of these assays, the target protein or the test substance is anchored onto a solid phase. The target protein/test compound complexes anchored on the solid phase can be detected at the end of the reaction. Generally, the target protein is anchored onto a solid surface, and the test compound (which is not anchored) can be labeled, either directly or indirectly, with detectable labels discussed herein.

It may be desirable to immobilize either the target protein, an anti-target protein antibody, or its target molecule to facilitate separation of complexed from uncomplexed forms of one or both of the proteins, as well as to accommodate automation of the assay. Binding of a test compound to a target protein, or interaction of a target protein with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase/target protein fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein. The mixture is then incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target protein binding or activity determined using standard techniques.

Other techniques for immobilizing a target protein on matrices include using conjugation of biotin and streptavidin. Biotinylated target protein can be prepared from biotin-NHS (N-hydroxy-succinimide) using techniques known in the art (e.g., biotinylation kit, Pierce Chemicals, Rockford, IU.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The complexes anchored on the solid surface can be detected in a number of ways. Where the previously non-immobilized component is pre-labeled, the presence of a label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some cases, the assay is performed utilizing antibodies reactive with target protein, but which do not interfere with binding of the target protein to its target molecule. Such antibodies can be derivatized to the wells of the plate, and unbound target protein trapped in the wells by antibody conjugation. Methods for detecting such complexes, in addition to those described above for the GST-immobilized complexes, include immunodetection of complexes using antibodies reactive with the target protein or target molecule, as well as enzyme-linked assays which rely on detecting an enzymatic activity associated with the target protein.

Alternatively, cell-free assays can be conducted in a liquid phase. In such an assay, the reaction products are separated from unreacted components, by any of a number of standard techniques, including but not limited to: differential centrifugation (see, for example, Rivas and Minton, Trends Biochem. Sci., 18:284-7, 1993); chromatography (gel filtration chromatography, ion-exchange chromatography); electrophoresis (e.g., Ausubel et al., eds. Current Protocols in Molecular Biology 1999, J. Wiley: New York.); and immunoprecipitation (see, for example, Ausubel et al., eds., 1999, Current Protocols in Molecular Biology, J. Wiley: New York). Such resins and chromatographic techniques are known to one skilled in the art (e.g., Heegaard, J. Mol. Recognit, 11: 141-148, 1998; Hage et al., J. Chromatogr. B. Biomed. Sci. Appl, 699:499-525, 1997). Further, fluorescence energy transfer may also be conveniently utilized, as described herein, to detect binding without further purification of the complex from solution.

The assay can include contacting the target protein or a biologically active portion thereof with a known compound that binds to the target protein to form an assay mixture, contacting the assay mixture with a test compound, and determining the ability of the test compound to interact with the target protein, wherein determining the ability of the test compound to interact with the target protein includes determining the ability of the test compound to preferentially bind to the target protein or biologically active portion thereof, or to modulate the activity of a target molecule, as compared to the known compound.

A target protein can, in vivo, interact with one or more cellular or extracellular macromolecules, such as proteins. For the purposes of this discussion, such cellular and extracellular macromolecules are referred to herein as "binding partners." Compounds that disrupt such interactions are useful for regulating the activity of the target protein. Such compounds can include, but are not limited, to molecules such as antibodies, peptides, and small molecules. In general, target proteins for use in identifying agents that disrupt interactions are the target proteins identified herein. In alternative embodiments, the invention provides methods for determining the ability of the test compound to modulate the activity of a target protein through modulation of the activity of a downstream effector of a target protein. For example, the activity of the effector molecule on an appropriate target can be determined, or the binding of the effector to an appropriate target can be determined, as described herein.

To identify compounds that interfere with the interaction between the target protein and its binding partner(s), a reaction mixture containing the target protein and the binding partner is prepared, under conditions and for a time sufficient, to allow the two products to form a complex. To test an inhibitory agent, the reaction mixture is provided in the presence (test sample) and absence (control sample) of the test compound. The test compound can be initially included in the reaction mixture, or can be added at a time subsequent to the addition of the target gene and its cellular or extracellular binding partner. Control reaction mixtures are incubated without the test compound or with a control compound. The formation of complexes between the target protein and the cellular or extracellular binding partner is then detected. The formation of a complex in the control reaction, and less formation of complex in the reaction mixture containing the test compound, indicates that the compound interferes with the interaction of the target protein and the interactive binding partner. Such compounds are candidate compounds for inhibiting the expression or activity or a target protein. Additionally, complex formation within reaction mixtures containing the test compound and normal target protein can also be compared to complex formation within reaction mixtures containing the test compound and mutant target gene product. This comparison can be important in those cases wherein it is desirable to identify compounds that disrupt interactions of mutant but not normal target protein. Binding assays can be carried out in a liquid phase or in heterogenous formats. In one type of heterogeneous assay system, either the target protein or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

In another embodiment, modulators of target expression (RNA or protein) are identified. For example, a cell or cell-free mixture is contacted with a test compound and the expression of target mRNA or protein evaluated relative to the level of expression of target mRNA or protein in the absence of the test compound. When expression of target mRNA or protein is greater in the presence of the test compound than in its absence, the test compound is identified as a stimulator (candidate compound) of target mRNA or protein expression. Alternatively, when expression of target mRNA or protein is less (statistically significantly less) in the presence of the test compound than in its absence, the test compound is identified as an inhibitor (candidate compound) of target mRNA or protein expression. The level of target mRNA or protein expression can be determined by methods described herein and methods known in the art such as Northern blot or Western blot for detecting target mRNA or protein.

In another aspect, the methods described herein pertain to a combination of two or more of the assays described herein. For example, a modulating agent can be identified using a cell-based or a cell-free assay, and the ability of the agent to modulate the activity of a target protein can be confirmed in vivo, e.g., in an animal such as an animal model for proteinopathy disease. This invention further pertains to novel agents identified by the above-described screening assays. Accordingly, it is within the scope of this invention to further use an agent (compound) identified as described herein (e.g., a target protein modulating agent, an anti-sense nucleic acid molecule, an siRNA, a target protein-specific antibody, or a target protein-binding partner) in an appropriate animal model to determine the efficacy, toxicity, side effects, or mechanism of action, of treatment with such an agent. Furthermore, novel agents identified by the above-described screening assays can be used for treatments as described herein. Compounds that modulate target protein expression or activity (target protein modulators) can be tested for their ability to affect metabolic effects associated with the target protein, e.g., with decreased expression or activity of target protein using methods known in the art and methods described herein. For example, the ability of a compound to modulate TDP-43 mediated cellular toxicity and aberrant protein aggregation can be tested using an in vitro or in vivo model for such disorders.

Target Protein Modulators

Methods of modulating target protein expression or activity can be accomplished using a variety of compounds including nucleic acid molecules that are targeted to a target nucleic acid sequence or fragment thereof, or to a target protein. Compounds that may be useful for inhibiting target protein expression or activity include polynucleotides, polypeptides, small non-nucleic acid organic molecules, small inorganic molecules, antibodies or fragments thereof, antisense oligonucleotides, siRNAs, and ribozymes. Methods of identifying such compounds are described herein.

RNA Inhibition (RNAi)

Molecules that are targeted to a target RNA are useful for the methods described herein, e.g., inhibition of target protein expression, e.g., for treating a proteinopathy such as ALS or Alzheimer's disease. Examples of nucleic acids include siRNAs. Other such molecules that function using the mechanisms associated with RNAi can also be used including chemically modified siRNAs and vector driven expression of hairpin RNA that are then cleaved to siRNA. The nucleic acid molecules or constructs that are useful as described herein include dsRNA (e.g., siRNA) molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, can transcribed be in vitro from a DNA template, or can be transcribed in vivo from, e.g., shRNA. The dsRNA molecules can be designed using methods known in the art, e.g., Dharmacon.com (see, siDESIGN CENTER) or "The siRNA User Guide," available on the Internet.

Negative control siRNAs ("scrambled") generally have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. Controls can also be designed by introducing an appropriate number of base mismatches into the selected siRNA sequence.

The nucleic acid compositions that are useful for the methods described herein include both siRNA and crosslinked siRNA derivatives. Crosslinking can be used to alter the pharmacokinetics of the composition, for example, to increase half-life in the body. Thus, the invention includes siRNA derivatives that include siRNA having two complementary strands of nucleic acid, such that the two strands are crosslinked. For example, a 3'OH terminus of one of the strands can be modified, or the two strands can be crosslinked and modified at the 3'OH terminus. The siRNA derivative can contain a single crosslink (e.g., a psoralen crosslink). In some cases, the siRNA derivative has at its 3' terminus a biotin molecule (e.g., a photocleavable biotin), a peptide (e.g., a Tat peptide to facilitate cellular uptake), a nanoparticle, a peptidomimetic, organic compounds (e.g., a dye such as a fluorescent dye), or dendrimer. Modifying SiRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions described herein can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished using methods known in the art, e.g., using the methods of Lambert et al., Drug Deliv. Rev., 47, 99-112, 2001 (describes nucleic acids loaded to polyalkylcyanoacrylate (PACA) nanoparticles); Fattal et al., J. Control Release, 53:137-143, 1998 (describes nucleic acids bound to nanoparticles); Schwab et al., Ann. Oncol., 5 Suppl. 4:55-8, 1994 (describes nucleic acids linked to intercalating agents, hydrophobic groups, polycations or PACA nanoparticles); and Godard et al., Eur. J. Biochem., 232:404-410, 1995 (describes nucleic acids linked to nanoparticles).

The nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the molecule can be radiolabeled, e.g., using H, P, or other appropriate isotope.

Synthetic siRNAs can be delivered into cells by cationic liposome transfection and electroporation. Sequences that are modified to improve their stability can be used. Such modifications can be made using methods known in the art (e.g., siSTABLET™, Dharmacon). Such stabilized molecules are particularly useful for in vivo methods such as for administration to a subject to decrease target protein expression. Longer term expression can also be achieved by delivering a vector that expresses the siRNA molecule (or other nucleic acid) to a cell, e.g., a neuronal, fat, liver, or muscle cell. Several methods for expressing siRNA duplexes within cells from recombinant DNA constructs allow longer-term target gene suppression in cells, including mammalian Pol III promoter systems (e.g., H1 or U6/snRNA promoter systems (Tuschl, Nature Biotechnol., 20:440-448, 2002) capable of expressing functional double-stranded siRNAs; (Bagella et al., J. Cell. Physiol, 177:206-1998; Lee et al., Nature Biotechnol., 20:500-505, 2002; Paul et al., Nature Biotechnol., 20:505-508, 2002; Yu et al., Proc. Natl. Acad. Sci. USA, 99(9):6047-6052, 2002; Sui et al., Proc. Natl. Acad. Sci. USA, 99(6):5515-5520, 2002). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998, supra; Lee et al., 2002, supra; Paul et al., 2002, supra; Yu et al., 2002, supra; Sui et al., 2002, supra). Constructs containing siRNA sequence under the control of T7 promoter also make functional siRNAs when cotransfected into the cells with a vector expression T7 RNA polymerase (Jacque, Nature, 418:435-438, 2002).

Animal cells express a range of noncoding RNAs of approximately 22 nucleotides termed micro RNA (miRNAs) and can regulate gene expression at the post transcriptional or translational level during animal development. miRNAs are excised from an approximately 70 nucleotide precursor RNA stem-loop. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng, Mol. Cell, 9:1327-1333, 2002). When expressed by DNA vectors containing polymerase III promoters, micro-RNA designed hairpins can silence gene expression (McManus, RNA 8:842-850, 2002). Viral-mediated delivery mechanisms can also be used to induce specific silencing of targeted genes through expression of siRNA, for example, by generating recombinant adenoviruses harboring siRNA under RNA Pol II promoter transcription control (Xia et al., Nat. Biotechnol., 20(10): 1006-10, 2002).

Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al, Proc. Natl. Acad. Sci. USA, 99: 14236-14240, 2002). In adult mice, efficient delivery of siRNA can be accomplished by "high-pressure" delivery technique, a rapid injection (within 5 seconds) of a large volume of siRNA containing solution into animal via the tail vein (Liu, Gene Ther., 6: 1258-1266, 1999; McCaffrey, Nature, 418:38-39, 2002; Lewis, Nature Genetics, 32:107-108, 2002). Nanoparticles and liposomes can also be used to deliver siRNA into animals. Likewise, in some embodiments, viral gene delivery, direct injection, nanoparticle particle-mediated injection, or liposome injection may be used to express siRNA in humans.

In some cases, a pool of siRNAs is used to modulate the expression of a target gene. The pool is composed of at least 2, 3, 4, 5, 8, or 10 different sequences targeted to the target gene. SiRNAs or other compositions that inhibit target protein expression or activity are effective for ameliorating undesirable effects of a disorder related to TDP-43 mediated toxicity when target RNA levels are reduced by at least 25%, 50%, 75%, 90%, or 95%. In some cases, it is desired that target RNA levels be reduced by not more than 10%, 25%, 50%, or 75%. Methods of determining the level of target gene expression can be determined using methods known in the art. For example, the level of target RNA can be determined using Northern blot detection on a sample from a cell line or a subject. Levels of target protein can also be measured using, e.g., an immunoassay method.

Antisense Nucleic Acids

Antisense nucleic acids are useful for inhibiting a target protein. Such antisense nucleic acid molecules comprise nucleic acid molecules whose nucleotide sequence is complementary to all or part of an mRNA encoding a target protein. An antisense nucleic acid molecule can also include sequences which are antisense to all or part of a non-coding region of the coding strand of a nucleotide sequence encoding a target protein. The non-coding regions ("5' and 3' untranslated regions") are the 5' and 3' sequences that flank the coding region and are not translated into amino acids. Based upon the nucleotide sequences disclosed herein, one of skill in the art can easily choose and synthesize any of a number of appropriate antisense molecules to target a gene described herein. For example, a "gene walk" comprising a series of contiguous oligonucleotides of 15-30 nucleotides spanning the length of a nucleic acid (e.g., a target nucleic acid) can be prepared, followed by testing for inhibition of expression of the gene. Optionally, gaps of 5-10 nucleotides can be left between the oligonucleotides to reduce the number of oligonucleotides synthesized and tested.

An antisense oligonucleotide can be, for example, about 5, 10, 15, 20, 25, 30, 35, 40, 45, or 50 nucleotides or more in length. An antisense nucleic acid described herein can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridin-e, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiour-acil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The new antisense nucleic acid molecules can be administered to a mammal, e.g., a human patient. Alternatively, they can be generated in situ such that they hybridize with or bind to cellular mRNA and/or genomic DNA encoding a selected polypeptide to thereby inhibit expression, e.g., by inhibiting transcription and/or translation. The hybridization can be by conventional nucleotide complementarities to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs can be used in which the antisense nucleic acid molecule is placed under the control of a strong pol II or pol III promoter.

An antisense nucleic acid molecule can be an alpha-anomeric nucleic acid molecule. An alpha-anomeric nucleic acid molecule forms specific double-stranded hybrids with complementary RNA in which, contrary to the usual, beta-units, the strands run parallel to each other (Gaultier et al., Nucleic Acids Res., 15:6625-6641, 1987). The antisense nucleic acid molecule can also comprise a 2'-o-methylribonucleotide (Inoue et al., Nucleic Acids Res., 15:6131-6148, 1987) or a chimeric RNA-DNA analog (Inoue et al., FEBS Lett., 215:327-330, 1987).

Antisense molecules that are complementary to all or part of a target gene described herein are also useful for assaying expression of such genes using hybridization methods known in the art. For example, the antisense molecule can be labeled (e.g., with a radioactive molecule) and an excess amount of the labeled antisense molecule is hybridized to an RNA sample. Unhybridized labeled antisense molecule is removed (e.g., by washing) and the amount of hybridized antisense molecule measured. The amount of hybridized molecule is measured and used to calculate the amount of expression of the target gene. In general, antisense molecules used for this purpose can hybridize to a sequence from a target gene under high stringency conditions such as those described herein. When the RNA sample is first used to synthesize cDNA, a sense molecule can be used. It is also possible to use a double-stranded molecule in such assays as long as the double-stranded molecule is adequately denatured prior to hybridization.

Ribozymes

Ribozymes that have specificity for a target nucleic acid sequence can also be used to inhibit target gene expression. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, Nature, 334:585-591, 1988)) can be used to catalytically cleave mRNA transcripts to thereby inhibit translation of the protein encoded by the mRNA. Methods of designing and producing ribozymes are known in the art (see, e.g., Scanlon, 1999, Therapeutic Applications of Ribozymes, Humana Press). A ribozyme having specificity for a target nucleic acid molecule or fragment thereof can be designed based upon the nucleotide sequence of a target cDNA. For example, a derivative of a Tetrahymena L-19 IVS RNA can be constructed in which the nucleotide sequence of the active site is complementary to the nucleotide sequence to be cleaved in a target RNA (Cech et al. U.S. Pat. No. 4,987,071; and Cech et al, U.S. Pat. No. 5,116,742). Alternatively, an mRNA encoding a target protein or fragment thereof can be used to select a catalytic RNA having a specific ribonuclease activity from a pool of RNA molecules (See, e.g., Barrel and Szostak, Science, 261:1411-1418, 1993).

Nucleic acid molecules that form triple helical structures can also be used to modulate target protein expression. For example, expression of a target protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene, Anticancer Drug Des., 6(6):569-84, 1991; Helene, Ann. N.Y. Acad. Sci., 660:27-36, 1992; and Maher, Bioassays, 14(12):807-15, 1992.

A nucleic acid molecule for use as described herein can be modified at the base moiety, sugar moiety or phosphate backbone to improve, e.g., the stability, hybridization, or solubility of the molecule. For example, the deoxyribose phosphate backbone of a nucleic acid can be modified to generate peptide nucleic acids (see Hyrup et al., Bioorganic & Medicinal Chem., 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., Proc. Natl. Acad. Sci. USA, 93: 14670-675, 1996.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup, 1996, supra; or as probes or primers for DNA sequence and hybridization (Hyrup, 1996, supra; Perry-O'Keefe et al., Proc. Natl. Acad. Sci. USA, 93: 14670-675, 1996).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., Nucleic Acids Res., 24:3357-63, 1996. For example, a DNA chain can be synthesized on a solid support using standard phosphoramidite coupling chemistry and modified nucleoside analogs. Compounds such as 5'-(4-methoxytrityl)amino~ 5'-deoxy-thymidine phosphoramidite can be used as a link between the PNA and the 5' end of DNA (Mag et al., Nucleic Acids Res., 17:5973-88, 1989). PNA monomers are then coupled in a stepwise manner to produce a chimeric molecule with a 5' PNA segment and a 3' DNA segment (Finn et al., Nucleic Acids Res., 24:3357-63, 1996). Alternatively, chimeric molecules can be synthesized with a 5' DNA segment and a 3' PNA segment (Peterser et al., Bioorganic Med. Chem. Lett., 5:1119-11124, 1975).

A nucleic acid targeting a target nucleic acid sequence can include appended groups such as peptides (e.g., for targeting host cell receptors in vivo), or agents facilitating transport across the cell membrane (see, e.g., Letsinger et al., Proc. Natl. Acad. Sci. USA, 86:6553-6556, 1989; Lemaitre et al., Proc. Natl. Acad. Sci. USA, 84:648-652, 1989; WO 88/09810) or the blood-brain barrier (see, e.g., WO 89/10134). In addition, oligonucleotides can be modified with hybridization-triggered cleavage agents (see, e.g., Krol et al., Bio/Techniques, 6:958-976, 1988) or intercalating agents (see, e.g., Zon, Pharm. Res., 5:539-549, 1988). To this end, the oligonucleotide may be conjugated to another molecule, e.g., a peptide, hybridization triggered cross-linking agent, transport agent, or a hybridization-triggered cleavage agent.

Polypeptides

Isolated target proteins, fragments thereof, and variants thereof are provided herein. These polypeptides can be used, e.g., as immunogens to raise antibodies, in screening methods, or in methods of treating subjects, e.g., by administration of the target proteins. An "isolated" or "purified" polypeptide or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of polypeptides in which the polypeptide of interest is separated from cellular components of the cells from which it is isolated or recombinantly produced. Thus, a polypeptide that is substantially free of cellular material includes preparations of polypeptides having less than about 30%, 20%, 10%, or 5% (by dry weight) of heterologous protein (also referred to herein as "contaminating protein"). In general, when the polypeptide or biologically active portion thereof is recombinantly produced, it is also substantially free of culture medium, i.e., culture medium represents less than about 20%, 10%, or 5% of the volume of the protein preparation. In general, when the polypeptide is produced by chemical synthesis, it is substantially free of chemical precursors or other chemicals, i.e., it is separated from chemical precursors or other chemicals that are involved in the synthesis of the polypeptide. Accordingly such preparations of the polypeptide have less than about 30%, 20%, 10%, or 5% (by dry weight) of chemical precursors or compounds other than the polypeptide of interest.

Expression of target proteins can be assayed to determine the amount of expression. Methods for assaying protein expression are known in the art and include Western blot, immunoprecipitation, and radioimmunoassay.

As used herein, a "biologically active portion" of a target protein includes a fragment of a target protein that participates in an interaction between a target protein and a non-target protein. Biologically active portions of a target protein include peptides including amino acid sequences sufficiently homologous to the amino acid sequence of a target protein that includes fewer amino acids than a full-length target protein, and exhibits at least one activity of a target protein. Typically, biologically active portions include a domain or motif with at least one activity of the target protein. A biologically active portion of a target protein can be a polypeptide that is, for example, 10, 25, 50, 100, 200 or more amino acids in length. Biologically active portions of a target protein can be used as targets for developing agents that modulate a target protein mediated activity, e.g., compounds that inhibit target protein activity.

In some embodiments, the target protein has a sequence identical to a sequence disclosed herein (e.g., an amino acid sequence found under a GenBank™ Accession Number listed in Table 1). Other useful polypeptides are substantially identical (e.g., at least about 45%, 55%, 65%, 75%, 85%, 95%, or 99% identical) to a sequence disclosed herein (e.g., an amino acid sequence found under a GenBank™ Accession Number listed in Table 1) and (a) retains the functional activity of the target protein yet differs in amino acid sequence due to natural allelic variation or mutagenesis, or (b) exhibits an altered functional activity (e.g., as a dominant negative) where desired. Provided herein are variants that have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the polypeptide. An antagonist of a polypeptide can inhibit one or more of the activities of the naturally occurring form of the polypeptide by, for example, competitively binding to a downstream or upstream member of a cellular signaling cascade that includes the polypeptide. Thus, specific biological effects can be elicited by treatment with a variant of limited function. Treatment of a subject with a variant having a subset of the biological activities of the naturally occurring form of the polypeptide can have fewer side effects in a subject relative to treatment with the naturally occurring form of the polypeptide. In some embodiments, the variant target protein is a dominant negative form of the target protein. Dominant negatives are desired, e.g., in methods in which inhibition of target protein action is desired. Also provided herein are chimeric or fusion proteins.

The comparison of sequences and determination of percent identity between two sequences is accomplished using a mathematical algorithm. The percent identity between two amino acid sequences is determined using the Needleman and Wunsch, J. Mol. Biol., 48:444-453, 1970) algorithm, which has been incorporated into the GAP program in the GCG software package (available on the Internet at gcg.com), using either a Blossum 62 matrix or a PAM250 matrix, and a gap weight of 16 and a length weight of 1. The percent identity between two nucleotide sequences is determined using the GAP program in the GCG software package (also available on the Internet at gcg.com), using a NWSgapdna.CMP matrix, a gap weight of 40, and a length weight of 1.

In general, percent identity between amino acid sequences referred to herein is determined using the BLAST 2.0 program, which is available to the public on the Internet at ncbi.nlm.nih.gov/BLAST. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al, Nucleic Acids Research 25:3389-3402, 1997.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a target protein is generally replaced with another amino acid residue from the same side chain family. Alternatively, mutations can be introduced randomly along all or part of a target protein coding sequence, such as by saturation mutagenesis, and the resultant mutants can be screened for target protein biological activity to identify mutants that retain activity. The encoded protein can be expressed recombinantly and the activity of the protein can be determined.

Antibodies

A target protein, or a fragment thereof, can be used as an immunogen to generate antibodies using standard techniques for polyclonal and monoclonal antibody preparation. The full-length polypeptide or protein can be used or, alternatively, antigenic peptide fragments can be used as immunogens. The antigenic peptide of a protein comprises at least 8 (e.g., at least 10, 15, 20, or 30) amino acid residues of the amino acid sequence of a target protein, and encompasses an epitope of a target protein such that an antibody raised against the peptide forms a specific immune complex with the polypeptide.

An immunogen typically is used to prepare antibodies by immunizing a suitable subject (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with a target protein as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, Nature, 256: 495-497, 1975, the human B cell hybridoma technique (Kozbor et al., Immunol. Today, 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, 30 1994, Coligan et al. (eds.) John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

As an alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., Bio/Technology, 9:1370-1372, 1991; Hay et al., Hum. Antibod. Hybridomas, 3:81-85, 1992; Huse et al., Science, 246:1275-1281, 1989; Griffiths et al., EMBO J., 12:725-734, 1993.

Additionally, recombinant antibodies, such as chimeric and humanized monoclonal antibodies, including both human and non-human portions, which can be made using standard recombinant DNA techniques, are provided herein. Such chimeric and humanized monoclonal antibodies can be produced by recombinant DNA techniques known in the art, for example using methods described in WO 87/02671; European Patent Application 184,187; European Patent Application 171,496; European Patent Application 173,494; WO 86/01533; U.S. Pat. No. 4,816,567; European Patent Application 125,023; Better et al., Science, 240:1041-1043, 1988; Liu et al., Proc. Natl. Acad. Sci. USA 84:3439-3443, 1987; Liu et al., J. Immunol, 139:3521-3526, 1987; Sun et al., Proc. Natl. Acad. Sci. USA, 84:214-218, 1987; Nishimura et al., Cane. Res., 47:999-1005, 1987; Wood et al., Nature, 314:446-449, 1985; and Shaw et al., J. Natl. Cancer Inst., 80:1553-1559, 1988); Morrison, Science, 229:1202-1207, 1985; Oi et al., Bio/Techniques, 4:214, 1986; U.S. Pat. No. 5,225,539; Jones et al., Nature, 321:552-525, 1986; Verhoeyan et al., Science, 239:1534, 1988; and Beidler et al., J. Immunol, 141:4053-4060, 1988.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a target protein. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (Int. Rev. Immunol, 13:65-93, 1995). A detailed discussion of this technology for producing human antibodies and human monoclonal antibodies and protocols for producing such antibodies is provided in U.S. Pat. No. 5,625,126; U.S. Pat. No. 5,633,425; U.S. Pat. No. 5,569,825; U.S. Pat. No. 5,661,016; and U.S. Pat. No. 5,545,806.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al., Biotechnology, 12:899-903, 1994).

An antibody directed against a target protein can be used to detect the polypeptide (e.g., in a cellular lysate or cell supernatant) to evaluate its abundance and pattern of expression. The antibodies can also be used diagnostically to monitor protein levels in tissue as part of a clinical testing procedure, e.g., for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Pharmaceutical Compositions

A test compound that has been screened by a method described herein and determined to modulate target protein expression or activity, can be considered a candidate compound. A candidate compound that has been screened, e.g., in an in vivo model of a proteinopathy such as Alzheimer's disease, and determined to have a desirable effect on the disorder, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions.

The compounds described herein that can modulate target protein expression or activity can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

Toxicity and therapeutic efficacy of such compounds can be determined using known pharmaceutical procedures in cell cultures or experimental animals (animal models of proteinopathies, e.g., Alzheimer's disease). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the $ED_{50}$ with little or no toxicity. The dosage may vary within this range depending upon the dosage form employed and the route of administration utilized. For a compound used as described herein (e.g., for treating a proteinopathy in a subject), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, generally between 2 to 8 weeks, between about 3 to 7 weeks, or for about 4, 5, or 6 weeks. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments.

For antibodies or a fragment thereof, the dosage is about 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible with such species-matched antibodies. Modifications such as lipidation can be used to stabilize antibodies and to enhance uptake and tissue penetration (e.g., into the brain). A method for lipidation of antibodies is described by Cruikshank et al. (J. Acquired Immune Deficiency Syndromes and Human Retrovirology, 14:193, 1997).

Compounds that modulate expression or activity of a target protein are described herein. Such a compound can be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Examples of doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

A nucleic acid molecule that is useful for modulating target protein expression or activity can be inserted into a vector and the resulting vector used as gene therapy vector.

Gene therapy vectors can be delivered to a subject by, for example, intravenous injection, local administration (see U.S. Pat. No. 5,328,470) or by stereotactic injection (see e.g., Chen et al. (Proc. Natl. Acad. Sci. USA, 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

Compounds described herein and those identified as described herein can be used to treat a subject that is at risk for or has a disease associated with TDP-43 mediated toxicity and/or the formation, deposition, accumulation, or persistence of aberrant protein aggregates. In certain embodiments, diseases include proteinopathies such as ALS, Alzheimer's disease, Huntington's disease, and fronto-temporal lobar degeneration (FTLD). An FTLD can be, e.g.: (i) FTLD with tau-positive inclusions such as FTLD with Pick bodies, corticobasal degeneration (CBD), progressive supranuclear palsy (PSP), or neurofibrillary tangle-only dementia; or (ii) FTLD with ubiquitin-positive, tau- and alpha-synuclein negative inclusions (UBI). (See, e.g., Kwong et al. (2007) Acta Neuropathol. 114:63-70). The proteinopathy can be a sporadic or familial (inherited) disorder (e.g., a sporadic or familial form of FTLD or ALS).

Methods of identifying an individual at risk for or having a proteinopathy are known in the art. Thus, methods and compositions for both prophylactic and therapeutic methods of treating a subject at risk of (or susceptible to) a proteinopathy are described herein. For example, an individual who is at risk of developing Alzheimer's disease (e.g., an individual whose family history includes Alzheimer's disease) and/or has signs he/she will develop Alzheimer's disease can be treated with the compounds and methods described herein.

As used herein, the term "treatment" is defined as the application or administration of a therapeutic compound to a patient, or application or administration of a therapeutic compound to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic compound includes, but is not limited to, small molecules such as small non-nucleic acid organic molecules, small inorganic molecules, peptides, synthetic peptides, antibodies, natural nucleic acid molecules (such as ribozymes, siRNAs, and antisense oligonucleotides), and molecules containing nucleic acid analogs.

Provided herein are methods for preventing in a subject (e.g., a human), a proteinopathy, by administering to the subject a target protein or a compound that modulates target protein expression or at least one target protein activity. Subjects at risk for a disease that is caused or contributed to by aberrant or unwanted target protein expression or activity can be identified by, for example, any or a combination of diagnostic or prognostic assays as described herein. Administration of a prophylactic compound can occur prior to the manifestation of symptoms characteristic of full-blown disease, such that the disease or disorder is prevented or, alternatively, delayed in its progression. Methods known in the art can be used to determine the efficacy of the treatment. The appropriate compound used for treating the subject can be determined based on screening assays described herein.

It is possible that some cases of proteinopathies are caused, at least in part, by an abnormal level of a target gene product, or by the presence of a target protein exhibiting abnormal activity. As such, the reduction in the level and/or activity of such gene products will bring about the amelioration of disorder symptoms.

As discussed, successful treatment of proteinopathies can be brought about by techniques that serve to inhibit the expression or activity of selected target gene products. For example, compounds, e.g., an agent identified using one or more of the assays described above, that proves to exhibit negative modulatory activity, can be used as described herein to prevent and/or ameliorate symptoms of proteinopathies. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and Fab, F(ab')2 and Fab expression library fragments, scFV molecules, and epitope-binding fragments thereof).

Further, siRNA, antisense, and ribozyme molecules that inhibit expression of a target gene can also be used in accordance with the methods described herein to reduce the level of target protein expression, thus effectively reducing the level of target protein activity. Triple helix molecules can be utilized to reduce the level of target protein activity.

Another method by which nucleic acid molecules can be utilized in treating or preventing a disease that can be treated by modulating target protein expression is through the use of aptamer molecules specific for target protein. Aptamers are nucleic acid molecules having a tertiary structure that permits them to specifically bind to protein ligands (e.g., Osborne, et al., Curr. Opin. Chem. Biol., 1: 5-9, 1997; and Patel, Curr. Opin. Chem. Biol., 1:32-46, 1997). Since nucleic acid molecules may be more conveniently introduced into target cells than therapeutic protein molecules may be, aptamers offer a method by which target protein activity can be specifically decreased without the introduction of drugs or other molecules that may have pluripotent effects.

An antibody that specifically recognizes a target protein can also be used. Lipofectin™ or liposomes can be used to deliver the antibody or a fragment of the Fab region that binds to the target protein in a cell. Where fragments of the antibody are used, the smallest inhibitory fragment that binds to the target antigen is generally used. For example, peptides having an amino acid sequence corresponding to the Fv region of the antibody can be used. Alternatively, single chain neutralizing antibodies that bind to an intracellular target protein can also be administered. Such single chain antibodies can be administered, for example, by expressing nucleotide sequences encoding single-chain antibodies within the target cell population (e.g., Marasco et al., Proc. Natl. Acad. Sci. USA, 90:7889-7893, 1993).

The identified compounds that inhibit target gene expression, synthesis and/or activity can be administered to a patient at therapeutically effective doses to prevent, treat, or ameliorate proteinopathies. A therapeutically effective dose refers to that amount of the compound sufficient to result in amelioration of symptoms of the disorders. Toxicity and therapeutic efficacy of such compounds can be determined by standard pharmaceutical procedures as described above.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound that is able to modulate target protein activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell et al., Current Opinion in Biotechnology, 7:89-94, 1996 and in Shea (Trends in Polymer Science, 2: 166-173, 1994). Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al. (Nature, 361:645-647, 1993). Through the use of isotope-labeling, the "free" concentration of compound that modulates the expression or activity of a target protein can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz et al., Analytical Chemistry, 67:2142-2144, 1995.

Target protein expression or activity can be modulated for therapeutic purposes. Accordingly, in some embodiments, the modulatory methods described herein involve contacting a cell with a compound that modulates one or more of the activities of a target protein associated with the cell. A compound that modulates target protein activity can be a compound as described herein, such as a nucleic acid or a protein, a naturally-occurring target molecule of a target protein (e.g., a target protein substrate or receptor), a target protein antibody, a target protein agonist or antagonist, a peptidomimetic of a target protein agonist or antagonist, or other small molecule.

In one embodiment, the compound stimulates one or more target protein activities. Examples of such stimulatory compounds include active target protein and a nucleic acid molecule encoding the target protein. In another embodiment, the compound inhibits one or more target protein activities. Examples of such inhibitory compounds include antisense target nucleic acid molecules, anti-target protein antibodies, and target protein inhibitors. These modulatory methods can be performed in vitro (e.g., by culturing cells with the compound and returning the cells to a subject) or, alternatively, in vivo (e.g., by administering the compound to a subject). As such, the new methods include treating an individual afflicted with a disease or disorder characterized by aberrant or unwanted expression or activity of a target protein or nucleic acid molecule. In one embodiment, the methods involve administering a compound (e.g., a compound identified by a screening assay described herein), or combination of compounds that modulate (e.g., up regulates or down regulates) target protein expression or activity. In another embodiment, the methods involve administering a target protein or nucleic acid molecule as therapy to compensate for reduced, aberrant, or unwanted target protein expression or activity.

Stimulation of target protein activity is desirable in situations in which target protein is abnormally downregulated and/or in which increased target protein activity is likely to have a beneficial effect. For example, stimulation of target protein activity is desirable in situations in which a target protein is downregulated and/or in which increased target protein activity is likely to have a beneficial effect. Likewise, inhibition of target protein activity is desirable in situations in which target protein is abnormally upregulated and/or in which decreased target protein activity is likely to have a beneficial effect.

In certain embodiments, one or more compounds (e.g., compounds that modulate expression or activity of different genes or proteins) can be administered, together (simultaneously) or at different times (sequentially). In addition, such compounds can be administered with another type(s) of compound(s) for treating a proteinopathy. For example, an identified compound may be administered together with agents typically used to treat the proteinopathy in question, e.g., donepezil hydrochloride (Aracept) for treatment of Alzheimer's disease.

It is clear from all the foregoing that the skilled person, based on the information provided herein, can design therapeutic agents which act as inhibitors, agonists, antagonists, etc. of TDP-43 modulator polypeptide activity. The elucidation of the role played by TDP-43, TDP-43 C-terminal variants and the TDP-43 activity modulators described herein in aberrant protein aggregation and cellular toxicity facilitates the development of pharmaceutical compositions useful for treatment and diagnosis of proteinopathies.

The following examples are provided to illustrate certain embodiments of the invention. They are not intended to limit the invention in any way.

Example 1

Identification of the Molecular Determinants of the C-Terminal Domain of TDP-43 which Mediate Aggregation and Toxicity An understanding of the sequence determinants within TDP-43 that govern its nuclear localization and eventual cytoplasmic aggregation enables the development of therapeutic strategies for a variety of proteinopathy disorders. The yeast based system provided below can be used to advantage to screen putative therapeutic agents for their ability to modulate TDP-43 mediated toxicity and protein aggregation.

The following materials and methods are provided to facilitate the practice of Example I.

Yeast Strains, Plasmids and Media

Yeast cells were grown in rich media (YPD) or in synthetic media lacking uracil and containing 2% glucose (SD/-Ura), raffinose (SRaf/-Ura), or galactose (SGal/-Ura). A TDP-43 Gateway entry clone was obtained from Invitrogen, containing full-length human TDP-43 in the vector pDONR221. A Gateway LR reaction was used to shuttle TDP-43 into Gateway-compatible yeast expression vectors (pAG vectors, (1), See the world wide web at addgene.org/yeast gateway). To generate C-terminally GFP-tagged TDP-43 constructs, a two-step PCR protocol was used to amplify TDP-43 (or truncated versions) without a stop codon and incorporate the Gateway attB1 and attB2 sites along with a Kozak consensus sequence. Resulting PCR products were shuttled into pDONR221 using a Gateway BR reaction. The entry clones (TDP-43$_{nostop}$ were then used in LR reactions with pAG426Gal-ccdB-GFP to generate the 2 μm TDP-43-GFP fusion constructs. To generate the integrating TDP-43-GFP construct, The TDP-43$_{nostop}$ entry clone was used in an LR reaction with pAG306GalccdB-GFP.

Two-micron plasmid constructs (e.g., pAG426Ga1-TDP-43-GFP) were transformed into BY4741 (MATa his3 leu2 met15 ura3). The TDP-43-GFP integrating strain was generated by linearizing pAG306Ga1-TDP-43-GFP by BsmI restriction digest, followed by transformation into the w303 strain (MATa can1-100, his3-11,15, leu2-3,112, trp1-1, ura3-1, ade2-1). The hsp104Δ and rnq1Δ strains are deletion mutants (gene disrupted by KanMX4) obtained from the haploid deletion collection (Invitrogen).

Yeast Transformation and Spotting Assays.

Yeast procedures were performed according to standard protocols (Guthrie et al. (2007) *Methods in Enzymology: Guide to Yeast Genetics and Molecular and Cell Biology* (Academic Press, NY, p 69). We used the PEG/lithium acetate method to transform yeast with plasmid DNA (Ito et al. (1983) *J. Bacteriol.* 153:163-168). For spotting assays, yeast cells were grown overnight at 30° C. in liquid media containing raffinose (SRaf/-Ura) until they reached log or mid-log phase. Cultures were then normalized for OD600, serially diluted and spotted onto synthetic solid media containing glucose or galactose lacking uracil and were grown at 30° C. for 2-3 days.

Semidenaturing Detergent-Agarose Gel Electrophoresis (SDD-AGE).

Ten-milliliter yeast cultures were grown for 6 h in SGal/-Ura to induce expression of TDP-43-YFP or Rnq1-YFP. Yeast cells were harvested and washed once with water. Cell pellets were resuspended in 300 μl of lysis buffer [100 mM Tris (pH 7.5), 200 mM NaCl, 1 mM EDTA, 5% glycerol, 1 mM DTT, NEM, PMSF, and protease inhibitor mixture]. Cell disruption was performed in a bead beater with an equal volume of acid-washed glass beads for 3 min at 4° C. Cellular debris was removed by low-speed spin (2 min at 315,000×g). Bradford assay was used to normalize protein concentrations and 4× sample buffer (2×TAE, 20% glycerol, 2, 4, or 8% SDS, bromophenol blue) was added to 1×, followed by incubation at room temperature for 10 min. Samples were subjected to gel electrophoresis (1.8% agarose in 1×TAE containing 0.1% SDS). Proteins were transferred to a nitrocellulose membrane (Hybond-C; Amersham) by using TBS as the transfer buffer and a semidry blotting unit (4 h). Proteins were detected by immunoblotting with an anti-GFP monoclonal antibody (Roche).

Sedimentation Assay.

Yeast cells were grown overnight in SRaf/-Ura and switched to SGal/-Ura to induce expression of each construct. Cells were incubated for 8 h and spheroplasts were prepared by incubating for 1 h at 37° C. in Spheroplasting buffer (1 M Sorbitol, 0.1 M EDTA 1 mg/ml zymolyase, 50 mM DTT). Cells were lysed in 200 μl of 1×TNE [500 mMTris.HCl (pH 7.5), 1.5 M NaCl, 20 mM EDTA, Roche protease inhibitor mixture]. Thirty microliters of lysate was incubated with 17 μl of 10×TNE, 40 μl of 10% SDS, and 133 μl of $dH_2O$ on ice for 5 min, followed by centrifugation for 1 h at 500×g in a Beckman OptiMax ultracentrifuge. Supernatant and pellet fractions were recovered and subjected to SDS/PAGE, followed by immunoblotting with an anti-GFP antibody (Roche).

Fluorescence Microscopy.

For fluorescence microscopy experiments, single-colony isolates of the yeast strains were grown to midlog phase in SRaf/-Ura media at 30° C. Cultures were spun down and resuspended in the same volume of SGal/-Ura to induce expression of the TDP-43 constructs. Cultures were induced with galactose for 4-6 h before being stained with DAPI to visualize nuclei and processed for microscopy. Images were obtained by using an Olympus IX70 inverted microscope microscope and a Photometrics CoolSnap HQ 12-bit CCD camera. Z-stacks of several fields were collected for each strain. The images were deblurred using a nearest neighbor algorithm in the Deltavision Softworx software and representative cells were chosen for figures.

Results

TDP-43 contains two RNA-recognition motifs (RRM1 and RRM2) and a glycine-rich region within the C-terminal region. To determine which regions within TDP-43 are necessary and sufficient for nuclear localization, aggregation, and/or toxicity, we generated a panel of TDP-43 truncations starting with the 2-μ plasmid, which produces toxic levels of the full-length protein (FIG. 1A). We expressed each of the truncated TDP-43 constructs as GFP fusions and determined their subcellular localization by fluorescence microscopy (FIG. 1B) and their effect on cell growth by spotting assays (FIG. 1C). By immunoblotting with either GFP- or TDP-43-specific antibodies, all of the fusion proteins were expressed at comparable levels.

Compared with full-length TDP-43, which formed multiple cytoplasmic aggregates, deletion of the C-terminus had a dramatic effect, resulting in an entirely nuclear localized protein (FIG. 1B, C-terminal deletion, construct d). Sub-deletions of the remaining N-terminal region, containing as few as the first 104 residues, wherein a weak nuclear localization sequence (NLS) is predicted to reside, were also localized to the nucleus. Moreover, a construct containing both RRMs but lacking the predicted NLS was diffusely distributed in the cytoplasm (FIG. 1B, N- and C-terminal deletion, construct e). Most of the C-terminal region was required for aggregation; addition of only a portion of the glycine-rich region immediately after RRM2 caused TDP-43 to now be distributed between both the nucleus and cytoplasm, but not aggregate (FIG. 1B, compare constructs k and l). Thus, sequences within the N-terminal portion of TDP-43 are necessary to direct nuclear localization, whereas the C-terminal region is required for cytoplasmic aggregation.

Having established that the C-terminal region is necessary for aggregate formation, we asked whether it was also sufficient. Surprisingly, a construct containing only the C-terminal portion was almost entirely diffusely localized within the cytoplasm, with occasional small cytoplasmic puncta (FIG. 1B, C-terminal region alone, construct j). Proteins containing larger fragments of RRM2 increased aggregate formation (FIG. 1B, compare constructs g-j); a construct containing the entire RRM2 along with the C-terminal region completely recapitulated the cytoplasmic aggregation pattern of full-length TDP-43 (FIG. 1B, compare constructs a and g). Thus, the TDP-43 C-terminal region alone is not sufficient for aggregation but, rather, requires an intact RRM for robust cytoplasmic foci formation indicating that RNA binding plays a role in aggregate formation and/or toxicity.

We performed spotting assays to determine which of the TDP-43 truncation constructs retained toxic potential (FIG. 1C). In addition to being required for aggregate formation, the C-terminal region was also necessary for cellular toxicity (FIG. 1C, compare constructs a and d). The C-terminal region, however, was not sufficient for toxicity. Rather, the entire RRM2 domain was also needed (FIG. 1C, compare constructs g-j). Nuclear localization was not required for toxicity, because construct f (lacks NLS) formed cytoplasmic aggregates (FIG. 1B) and was toxic (FIG. 1C). Aggregation per se was not sufficient for toxicity because construct h was not toxic, despite significant aggregation. Taken together, these data indicate that the RNA recognition motif and C-terminal region are together required for TDP-43 to form toxic aggregates. Thus, we have defined the sequence requirements for TDP-43 aggregation and cellular toxicity in vivo. It is noteworthy that the particular toxic fragment we have defined (construct g) is nearly a perfect match to one of the recently reported caspase-dependent cleavage fragments of TDP-43 (Zhang et al. (2007) J. Neurosci 27:10530-10534), thus providing a mechanistic link between the presence of aggregating TDP-43 cleavage products and cellular pathology.

In view of these results, it is clear that either full length TDP-43 protein or the functional C-terminal variant encoded by construct g described above can be utilized in the screening assays described above for the identification of agents which modulate the activity of TDP-43 or the activity modulators thereof described below in Example 2.

Example 2

Identification and Characterization of TDP-43 Activity Modulator Proteins Associated with Aberrant Protein Aggregation and Cellular Toxicity The yeast model system described in Example 1 is useful to monitor early events in TDP-43 aggregation and toxicity. The identification of genes and signaling pathways associated with suppression or enhancement of TDP-43 toxicity will provide insight into why TDP-43 is toxic in the first place. In previous studies, we have successfully employed a similar approach with the Parkinson's disease protein, α-synuclein (Cooper et al. (2006) Science 313:324-328; Gitler et al. (2008) Proc Natl Acad Sci 105:145-150). We performed genetic screens for α-synuclein toxicity modifiers and identified ER-Golgi vesicular trafficking genes (e.g. Ypt1, Ykt6, Gyp8, Sec22, Sec28) as potent modifiers. This suggested that α-synuclein might be toxic to yeast cells because it inhibited vesicular transport between the ER and Golgi. Indeed, cell biological experiments confirmed this hypothesis in vivo and studies in animal models validated the relevance of our discovery in yeast to dopaminergic neurons, a disease-relevant cell type.

Figure 2:
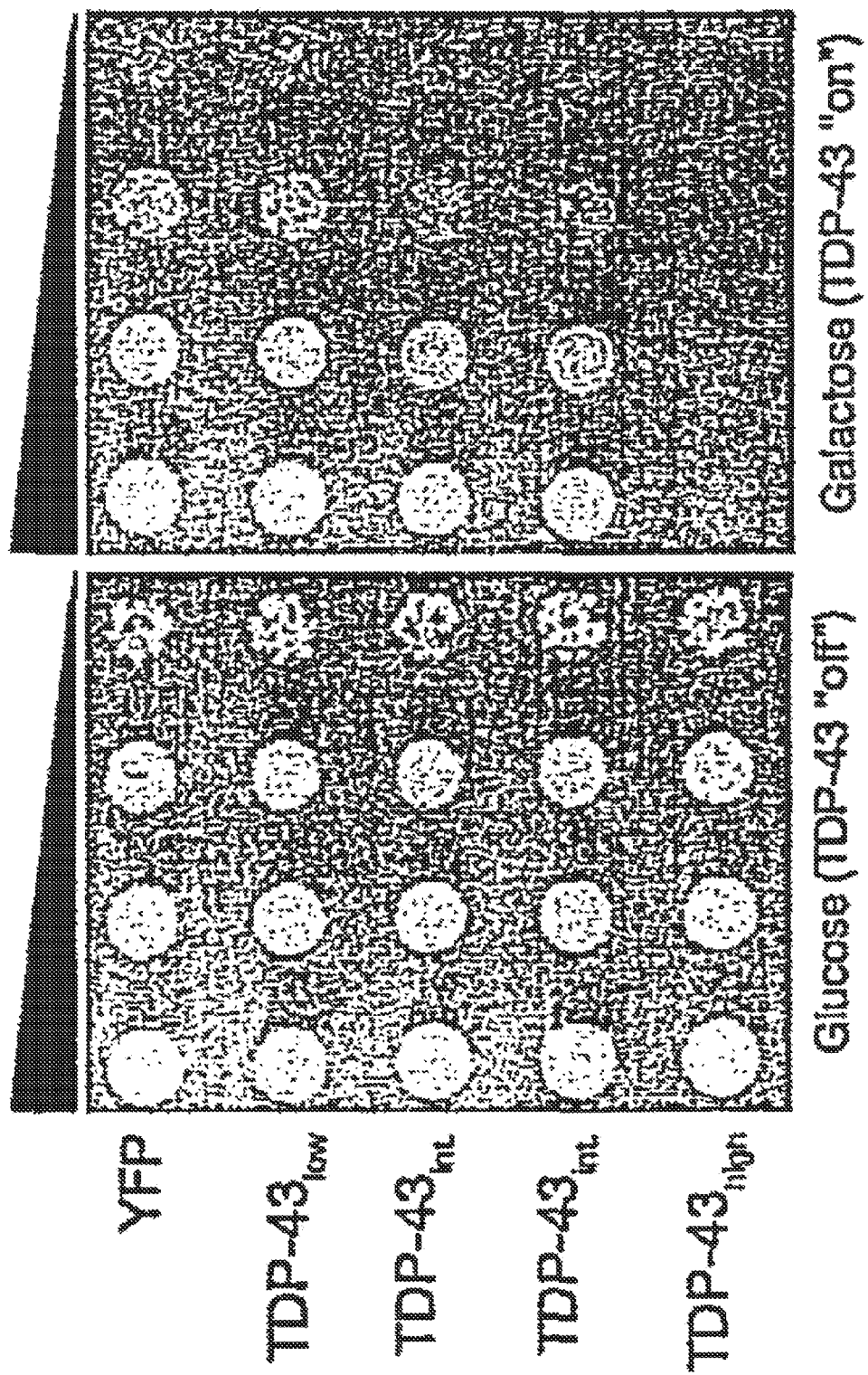
FIG. 2: Yeast strains engineered to express various levels of TDP-43. Spotting assays demonstrate galactose inducible expression of YFP alone or low, intermediate, and high levels of TDP-43 expression which result in a corresponding level of toxicity.

In the present example, we describe performance of similar yeast screens to identify nucleic acids encoding protein modulators of TDP-43 aggregation and toxicity which are readily validated in human patient samples or animal models. A critical component of our screening approach is our ability to regulate TDP-43 expression levels, producing various degrees of toxicity in transgenic organisms of choice. For our gene deletion screen, we chose a nontoxic or slightly toxic level of TDP-43 expression, thereby facilitating identification of gene knockouts that enhance toxicity. On the other hand, for the plasmid overexpression screen, an intermediate level of expression is desirable, permitting the identification of suppressors as well as enhancers of toxicity. Finally, a high toxicity strain will be useful for testing the strengths of our various hits. Accordingly, low, intermediate, and high-toxicity TDP-43 strains have been constructed. See FIGS. 2 and 3. We are thus able to deploy at will strains with varying levels of TDP-43 expression, depending on the requirements of the individual experiment.

Screening Yeast Gene Deletions for Modulators of TDP-43 Aggregation and Toxicity We utilize a Singer ROTOR HDA robot designed specifically for yeast synthetic genetic array (SGA) analysis. We have condensed the yeast deletion library (MATα-4,850 strains) from 52 plates down to a stack of 13 plates (384 strains in duplicate=768 colonies per plate). To analyze results from these screens, we implemented colony analysis software and developed several custom Excel macros to organize and sort results.

Figure 4:
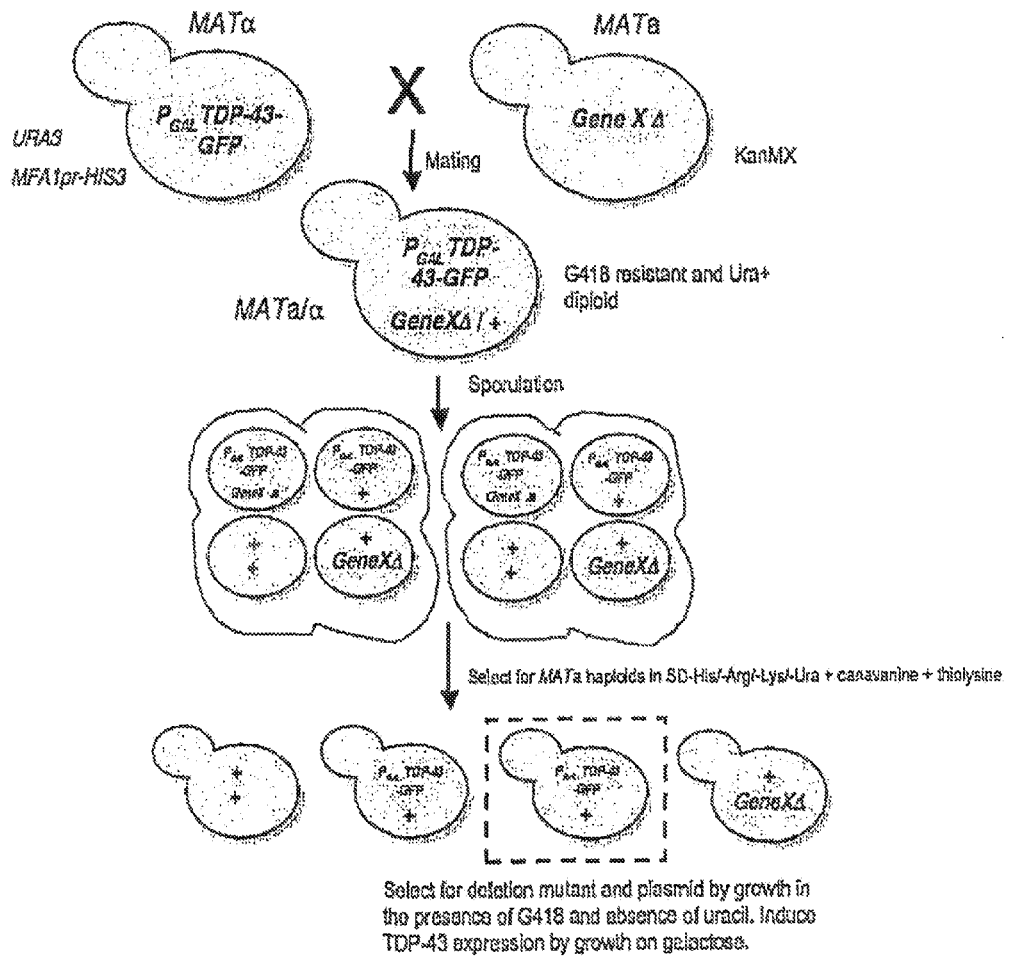
FIG. 4: A schematic diagram of a TDP-43 synthetic lethal screen.

A high-throughput method to rapidly perform synthetic lethal screens in yeast (referred to as synthetic genetic array (SGA) analysis) has been previously described (Tong et al. (2001) Science 294: 2364-2368). A schematic diagram of the screen is provided in FIG. 4. Haploid MATα cells harboring our integrated galactose-inducible TDP-43-GFP expression cassette were utilized as the starting "query" strain. The TDP-43 expression cassette in this strain is linked to a dominant selectable marker, URA3, which allows cells to grow in the absence of uracil, as well as the MFAlpr-HIS3 reporter (only expressed in MATa cells). To begin the screen, the MATα query strain was arrayed onto four YPD (rich media) agar plates at 768-colony density and grown overnight at 30° C. Next, the library of ~4,850 MATa viable yeast deletion mutants (Yeast Deletion Collection, Invitrogen), each carrying a gene deletion mutation linked to a G418-resistance marker (KanMX), at 768-colony density (384 individual knockout strains per plate, in duplicate), was arrayed onto YPD agar plates containing G418, thus creating a deletion mutant array (DMA). The yeast DMA is comprised of 13 plates containing the entire library of non-essential gene deletions. These plates are also incubated overnight at 30° C. The query strain is then mated with the DMA by first pinning the 768-format query strain onto 13 fresh YPD plates, and then pinning the DMA on top of the query cells. The mating plates are then incubated at room temperature for 1 day. Diploids are selected by pinning MATa/zygotes onto glucose-containing synthetic solid media containing G418 and lacking uracil (SDI-Ura+G418) and incubating at 30° C. for two days. The heterozygous diploids that survive this selection are then transferred to enriched sporulation plates (low levels of carbon and nitrogen) and incubated at ~22° C. for five days. The resulting spores are then transferred into synthetic medium lacking histidine, which will selectively germinate the MATa meiotic progeny (because they express the MFAlpr-HIS3 reporter), and incubated at 30° C. for two days. After another round of pinning onto the same plates, to enrich for MATa haploids, the MATa meiotic progeny are transferred, by pinning, to agar plates containing G418 and glucose but lacking uracil, which selects for growth of mutant haploids harboring TDP-43-GFP, but keeps its expression off. Following incubation at 30° C. for two days, each of the 13 plates are digitally photographed. Colonies on these plates will serve as growth controls (mutant, TDP-43-GFP expression off). Finally, colonies are pinned to agar plates containing G418 and galactose, which turns on TDP-43-GFP expression, and incubated at 30° C. for two days. These plates are then photographed and image analysis software (Collins et al. (1998) Genome Biol. 7:R63) employed to measure colony size. Colony sizes of the mutant+TDP-43-GFP "on" cells are then compared to the mutant+TDP-43-GFP "off" cells in order to assess the effect of the double-mutant combinations on growth rate and viability. To account for potential differences between cell growth on glucose vs. galactose, the screen is also performed in parallel with a wild-type query strain harboring a galactose-regulated GFP-alone expression cassette at the URA3 locus. Each screen is performed 3 independent times for a total of 6 replicates (the strains are in duplicate on each plate).

Figure 7:
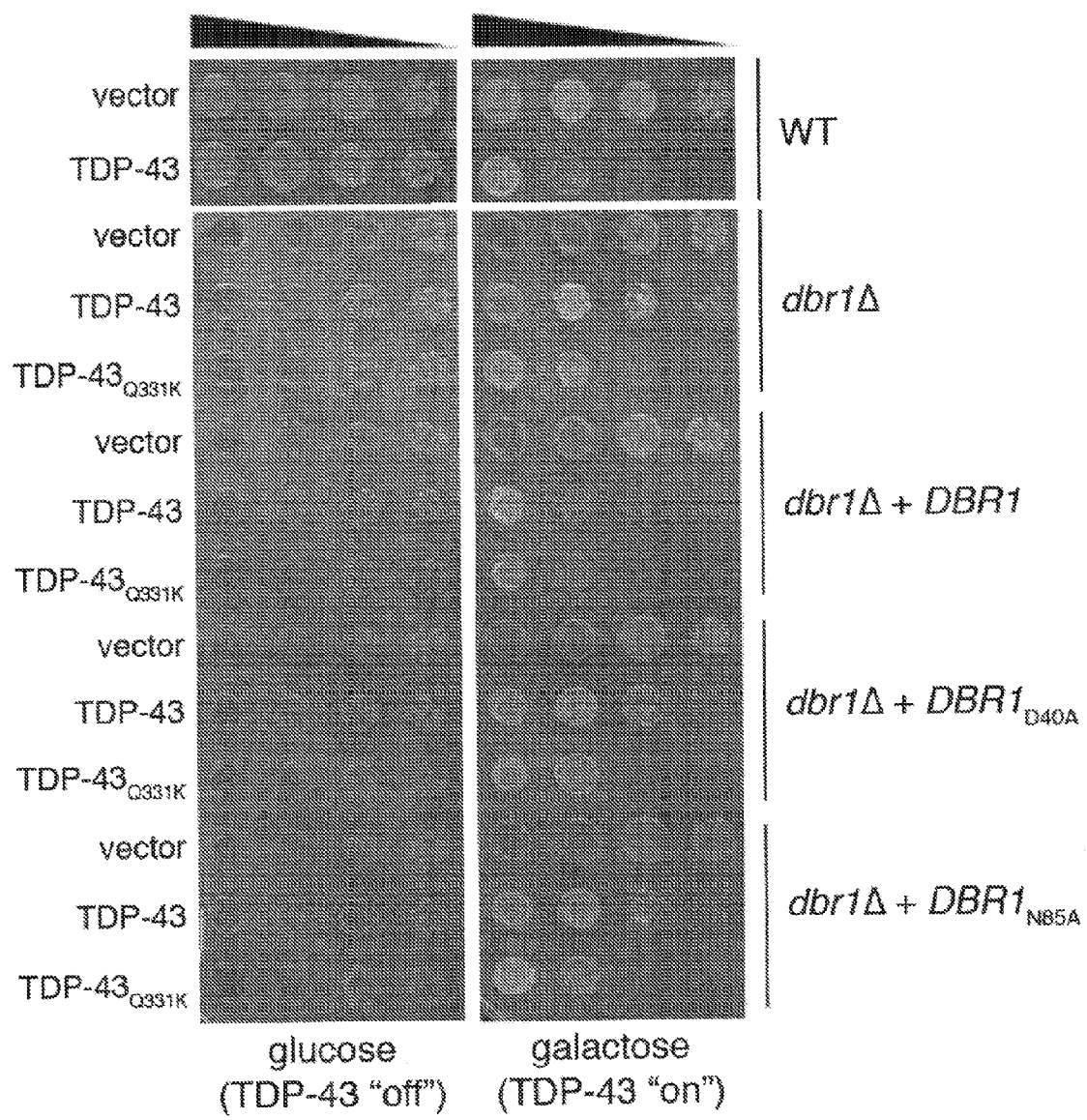
FIG. 7: Plates showing that DBR1 debranching activity is required for TDP-43 toxicity. Spotting assays show WT TDP-43 or an ALS-linked mutant TDP-43 (Q331K) are toxic in WT cells but not in dbr1Δ cells. Expressing WT DBR1 from a plasmid restores the toxicity, however expressing point mutants of DBR1 that abolish debranching activity but keep the rest of the protein intact (e.g. D40A, N85A) do not restore activity, indicating that the debranching activity of DBR1 is required for TDP-43 toxicity and suggesting that compounds which inhibit this activity could be effective at reversing toxic effects of TDP-43.

The yeast gene deletions that enhance toxicity, (e.g., TIF4631, MRPL39, FLD1, MSN2, PBL16B and NHX1) are verified by independent transformations and/or random spore analysis. The same collection of mutants has also been scored for effects on aggregation. For this analysis, each deletion expressing TDP-43-GFP, was be grown overnight in selective liquid media and then switched to galactose-containing media to induce TDP-43 expression. Following incubation for 3-6 hours, cells were visualized by fluorescence microscopy and the percentage of cells with inclusions as well as the average number of inclusions per cell is determined. For the initial visual screen, cells are scored rapidly at low power (400×) on an Olympus 1×70 inverted microscope. Promising candidates are also assessed under high power (1000×). Agents which increase the expression levels of these proteins should have efficacy for the treatment of proteinopathy disorders. The yeast deletions that suppress toxicity (e.g., SET3, DBR1, CCE1, SIW14, YDR067C, DOM34, MGD1 and RPL16) were also verified. The results shown in FIG. 7 demonstrate that DBR1 debranching activity is required for TDP-43 toxicity. Spotting assays show WT TDP-43 or an ALS-linked mutant TDP-43 (Q331K) are toxic in WT cells but not in dbr1Δ cells. Expressing WT DBR1 from a plasmid restores the toxicity, however expressing point mutants of DBR1 that abolish debranching activity but keep the rest of the protein intact (e.g. D40A, N85A) do not restore activity, indicating that the debranching activity of DBR1 is required for TDP-43 toxicity and indicating that compounds which inhibit this activity could be effective at reversing toxic effects of TDP-43. Indeed, siRNA which inhibit DBR1 activity are being tested as therapeutics for the treatment of HIV. See Ye et al. (2005) *Retrovirology* 2005, 2:63. Such inhibitory siRNAs may also have efficacy for the treatment of proteinopathies used alone or in conjunction with conventional agents used to treat these disorder. Agents which inhibit the activity of the expression or function of the other suppressors identified in the deletion screen should also inhibit TDP-43 proteinopathies. Table 1 provides the results from this deletion screen.

| Effect | ORF name | Symbol | Other symbol | Function | Yeast Amino Acid Acc No | Human Homolog | Human Amino Acid Acc No | Human Nucleic Acid Acc No |
|---|---|---|---|---|---|---|---|---|
| suppressor | YKR029C | SET3 | | Defining member of the SET3 histone deacetylase complex which is a meiosis-specific repressor of sporulation genes; necessary for efficient transcription by RNAPII; one of two yeast proteins that contains both SET and PHD domains | NP_012954 | ASH1 | NP_060959.2 | NM_018489.2 |
| suppressor | YKL149C | DBR1 | | RNA lariat debranching enzyme, involved in intron turnover; required for efficient Ty1 transposition | NP_012773 | DBR1 | NP_057300.2 | NM_016216.2 |
| enhancer | YGR162W | TIF4631 | PRP26 | Translation initiation factor eIF4G, subunit of the mRNA cap-binding protein complex (eIF4F) that also contains eIF4E (Cdc33p); associates with the poly(A)-binding protein Pab1p, also interacts with eIF4A (Tif1p); homologous to Tif4632p | NP_011678 | EIF4G1 | NP_004944.2 | NM_004953.3 |
| enhancer | YML009C | MRPL39 | | Mitochondrial ribosomal protein of the large subunit | NP_013705 | MRPL33 | NP_004882.1 | NM_004891.3 |
| suppressor | YKL011C | CCE1 | MGT1 | Mitochondrial cruciform cutting endonuclease, cleaves Holliday junctions formed during recombination of mitochondrial DNA | NP_012914 | none | none | none |
| enhancer | YLR404W | FLD1 | SEI1 | Seipin protein involved in lipid droplet morphology, number, and size; proposed to be involved in lipid metabolism; related to the human BSCL2 which is associated with lipodystrophy | NP_013508 | none | none | none |
| enhancer | YMR037C | MSN2 | | Transcriptional activator related to Msn4p; activated in stress conditions, which results in translocation from the cytoplasm to the nucleus; binds DNA at stress response elements of responsive genes, inducing gene expression | NP_013751 | none | none | none |
| suppressor | YNL032W | SIW14 | OCA3 | Tyrosine phosphatase that plays a role in actin filament organization and endocytosis; localized to the cytoplasm | NP_014366 | none | none | none |
| suppressor | YDR067C | YDR067C | | Cytoplasmic protein required for replication of Brome mosaic virus in *S. cerevisiae*, which is a model system for studying replication of positive-strand RNA viruses in their natural hosts | NP_010352 | none | none | none |
| suppressor | YNL001W | DOM34 | possibly DOM34 | Endoribonuclease; functions in no-go mRNA decay, protein translation to promote G1 progression nd differentiation, required for meiotic cell division; similar to the eukaryotic Pelota | NP_014397 | PELO | NP_057030.3 | NM_015946.4 |
| suppressor | YNL173C | MDG1 | | Plasma membrane protein involved in G-protein mediated pheromone signaling pathway; overproduction suppresses bem1 mutations | NP_014226 | PRKAB2 | NP_005390.1 | NM_005399.3 |
| suppressor | YIL133C | RPL16A | RPL13 | N-terminsuppressory acetylated protein component of the large (60S) ribosomal subunit, binds to 5.8 S rRNA; has similarity to Rpl16Bp, *E. coli* L13 and rat L13a ribosomal proteins; transcriptionsuppressory regulated by Rap1p | NP_012133 | RPL13A | NP_036555.1 | NM_012423.2 |
| enhancer | YNL069C | RPL16B | RP23 | N-terminsuppressory acetylated protein component of the large (60S) ribosomal subunit, binds to 5.8 S rRNA; has similarity to Rpl16Ap, *E. coli* L13 and rat L13a ribosomal proteins; transcriptionsuppressory regulated by Rap1p | NP_014330 | RPL13A | NP_036555.1 | NM_012423.2 |
| enhancer | YDR456W | NHX1 | VPL27/NHA2/VPS44 | Endosomal Na+/H+ exchanger, required for intracellular sequestration of Na+; required for osmotolerance to acute hypertonic shock | NP_010744 | SLC9A6 | NP_001036002.1 | NM_001042537.1 |

Over-Expression Screen

Figure 5:
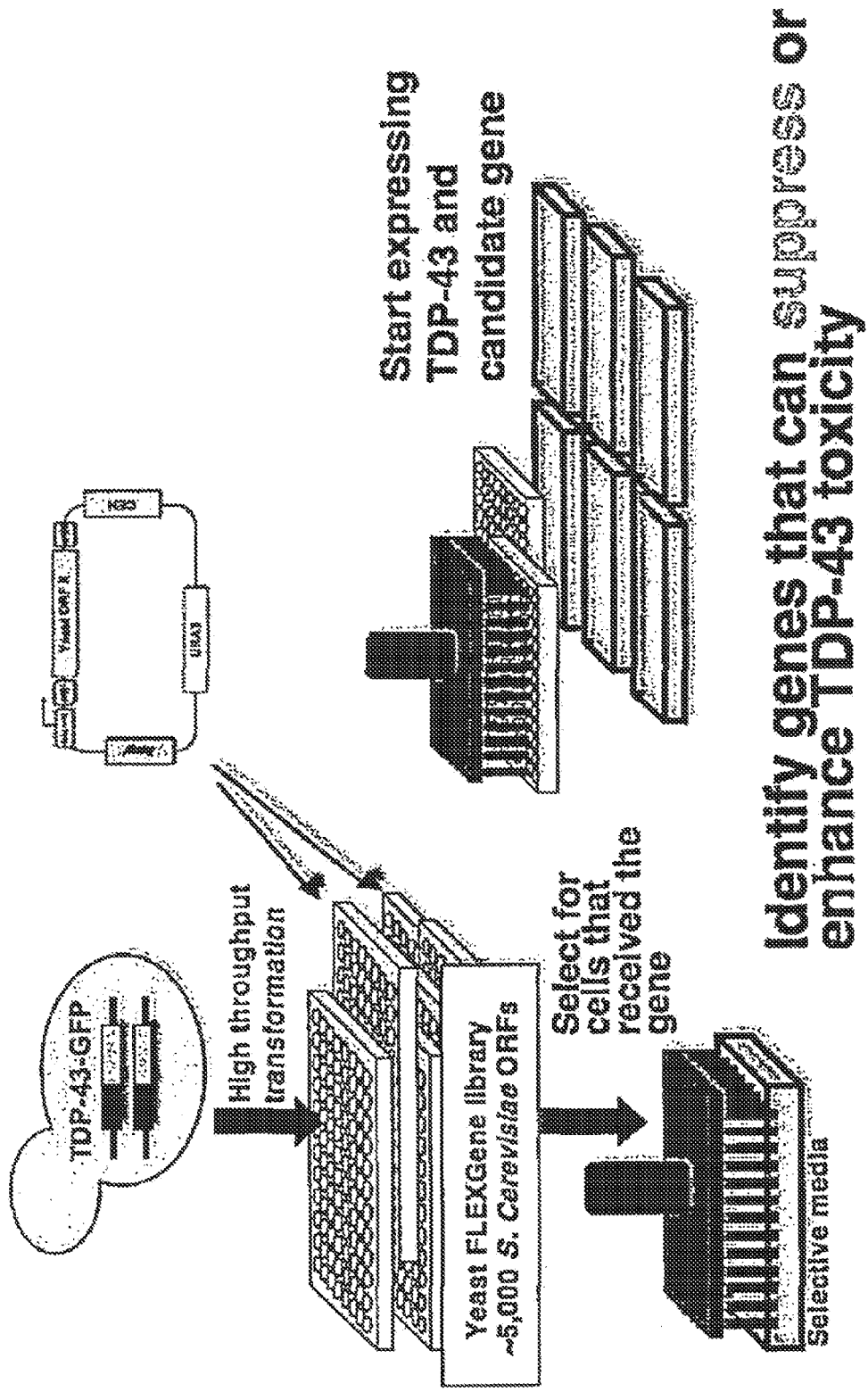
FIG. 5: A schematic diagram of a TDP-43 over-expression screen.

The deletion screen described above may not identify all of the important molecules involved in TDP-43 aggregation and toxicity. For example, if a knockout were lethal, the clone would not be present in the strains examined, since it is a collection of 4,850 non-lethal mutations. Our yeast FLEX-Gene overexpression library will allow us to survey >5,000 yeast open reading frames, including essential genes (FIG. 5). For this screen, we will employ a slightly different galactose-inducible integrated TDP-43-GFP yeast strain than what we will use for the synthetic lethal screen. Because we want to identify both suppressors and enhancers of TDP-43 toxicity, we employed a galactose-inducible TDP-43-GFP strain that has an intermediate level of toxicity, owing to the locus in which TDP-43 was integrated (HIS3 vs. URA3). Our yeast plasmid library is comprised of sixty 96-well microtiter plates, with each well containing a single sequence-verified yeast expression plasmid. Control plasmids are also distributed throughout the library. We have our library in two formats: 1) bacterial glycerol stocks and 2) Qiagen miniprep DNA. The plasmid DNAs will be used for the yeast transformation and the bacterial glycerol stocks will be our permanent back-up source, used to replenish the DNA copy and for cherry-picking putative hits for re-testing.

To begin the screen, plasmid DNA is added to new 96-well plates and dried overnight in the hood. We modified the standard PEG/LiOAc yeast transformation protocol for use with high-throughput screens (Cooper et al. (2006) Science 313: 324-328). A BioRobot RapidPlate liquid handling robot that precisely aliquots, mixes, and transfers cells or liquids to 96 wells at a time is employed for this purpose. We will use the RapidPlate during each step of the transformation procedure. The TDP-43 query strain is grown overnight in 2 liters YPD until mid log phase. Yeast cells are then harvested by centrifugation, washed with water and treated with 0.1 M LiOAc. Boiled salmon sperm DNA is added to the cells and 50 µl yeast 1 LiOAc mixture aliquoted to each plasmid-containing DNA plate. Following a 30-minute incubation at room temperature, a mixture of PEG/LiOAc/DMSO is added to each sample and mixed. Following another 30-minute incubation at room temperature, the yeast cells are heat shocked at 42° C. for 15 minutes. After heat shock, the yeast cells are pelleted, washed once with SDI-Ura liquid media, resuspended in 200 µl SDI-Ura, and allowed to recover for 2 days at 30° C. The library plasmids contain the URA3 selectable marker and our query strain is auxotrophic for uracil, thus only yeast cells that harbor a plasmid are able to grow. Transformants are transferred to fresh 96-well plates containing raffinose as the carbon source and grown for 24 hours. Growth in raffinose removes glucose repression but does not induce galactose-regulated gene expression, thus poising our cells to express both TDP-43 and the gene of interest immediately upon the addition of galactose. Transformants grown in raffinose are spotted onto either galactose- or glucose-containing agar plates, incubated for 2-3 days, photographed, and genes that cause TDP-43-expressing cells to grow better (toxicity suppressors) or worse (toxicity enhancers) identified. The glucose plates serve as controls for transformation and spotting efficiency. This procedure is repeated for six consecutive days, 10 plates per day, until all >5,000 of the yeast plasmids are transformed and their effect on TDP-43 toxicity assessed. To help eliminate potential false-positives, we will perform the entire screen three times, with independent transformations. Effects of modifier genes on TDP-43 aggregation will be assessed exactly as for the synthetic lethal screen hits.

We picked the genes from our library of >5,000 yeast ORFs (96 genes per plate×10 plates). Examples of plates from an exemplary screen are shown in FIG. 3. We repeated the screen twice and verified cherry picked hits at least 3 additional times. Table 2 shows the hits from this screen. The fact that the hits we are getting from this screen are non-overlapping with our previous α-syn screen indicates the specificity of the screen. The major functional categories of hits from the pilot TDP-43 screen include RNA-binding proteins, and regulators of RNA metabolism. This is very different from our α-syn screen, which identified mainly vesicle trafficking genes. Thus, rather than identifying hits that simply functioned in a very general way to rescue cells from misfolded proteins (e.g. general stress responses), we are able to model specific aspects of the underlying biology of these disease proteins (for example vesicle trafficking with α-syn and RNA metabolism with TDP-43).

TABLE 2

| Strength | Type | Systematic Name | Gene Name | Yeast Amino Acid Acc No | Function | Description | Human Homolog | Human Amino Acid Acc No | Human Nucleic Acid Acc No |
|---|---|---|---|---|---|---|---|---|---|
| 2 | suppressor | YLL026W | HSP104 | NP_013074 | chaperone | Heat shock protein that cooperates with Ydj1p (Hsp40) and Ssa1p (Hsp70) to refold and reactivate previously denatured, aggregated proteins; responsive to stresses including: heat, ethanol, and sodium arsenite; involved In [PSI+] propagation | none | none | none |
| 2 | suppressor | YKL171W | YKL171W | NP_012750 | kinase | Putative protein of unknown function; predicted protein kinase; implicated in proteasome function; epitope-tagged protein localizes to the cytoplasm | doublecortin and CaM kinase-like 1 | NP_004725.1 | NM_004734.3 |
| 1 | suppressor | YGR052W | FMP48 | NP_011566 | kinase | Putative protein of unknown function; the authentic, non-tagged protein is detected in highly purified mitochondria in high-throughput studies | serine/threonine kinase 36 | NP_056505.2 | NM_015690.3 |
| 3 | suppressor | YFL033C | RIM15 | NP_116620 | kinase | Glucose-repressible protein kinase involved in signal transduction during cell proliferation in response to nutrients, specifically the establishment of stationary phase; identified as a regulator of IME2; substrate of Pho80p-Pho85p kinase | serine/threonine kinase 38 | NP_009202.1 | NM_007271.2 |
| -3 | enhancer | YBR136W | MEC1 | NP_009694 | kinase | Genome integrity checkpoint protein and PI kinase superfamily member; signal transducer required for cell cycle arrest and transcriptional responses prompted by damaged or unreplicated DNA; monitors and participates in meiotic recombination | ataxia telangiectasia and Rad3 related protein | NP_001175.2 | NM_001184.3 |
| -3 | enhancer | YER129W | SAK1 | NP_011055.1 | kinase | Upstream kinase for the SNF1 complex; partially redundant function with Elm1p and Tos3p; members of this family of kinases have functional orthology with LKB1, a mammalian kinase associated with Peutz-Jeghers cancer-susceptibility syndrome | calcium/calmodulin-dependent protein kinase | NP_115670.1 | NM_032294.2 |
| -3 | enhancer | YNL154C | YCK2 | NP_014245 | kinase | Palmitoylated, plasma membrane-bound casein kinase I isoform; shares redundant functions with Yck1p in morphogenesis, proper septin assembly, endocytic trafficking; provides an essential function overlapping with that of Yck1p | casein kinase 1 gamma 2, isoform CRA_a; casein kinase1, gamma 3 isoform 2 | NP_001038188.1 | NM_004384.3 |
| -2 | enhancer | YDR247W | VHS1 | NP_010533 | kinase | Cytoplasmic serine/threonine protein kinase; identified as a high-copy suppressor of the synthetic lethality of a sis2 sit4 double mutant, suggesting a role in G1/S phase progression; homolog of Sks1p | MAP/microtubule affinity-regulating kinase 2 | NP_001034557.1 | NM_001039468.1 |
| -1 | enhancer | YAR018C | KIN3 | NP_009410 | kinase | Nonessential protein kinase with unknown cellular role | NIMA (never in mitosis gene a)-related kinase 2 | NP_003148.2 | NM_003157.3 |
| -3 | enhancer | YER059W | PCL6 | NP_010980 | kinase | Pho85p cyclin of the Pho80p subfamily; forms the major Glc8p kinase together with Pcl7p and Pho85p; involved in the control of glycogen storage by Pho85p; stabilized by Elongin C binding | none | none | none |
| -3 | enhancer | YIL156W | UBP7 | NP_012110 | protease | Ubiquitin-specific protease that cleaves ubiquitin-protein fusions | ubiquitin specific peptidase 21 | NP_001014443.1 | NM_001014443.2 |
| 2 | suppressor | YOR198C | BFR1 | NP_014841 | RNA binding | Component of mRNP complexes associated with polyribosomes; implicated in secretion and nuclear segregation; multicopy suppressor of BFA (Brefeldin A) sensitivity | none | none | none |
| 1 | suppressor | YOR359W | VTS1 | NP_015004 | RNA binding | Post-transcriptional gene regulator, RNA-binding protein containing a SAM domain; shows genetic interactions with Vti1p, which is a v-SNARE Involved in cis-Golgi membrane traffic | sterile alpha motif domain containing 4B | NP_060498.2 | NM_018028.2 |
| 2 | suppressor | YLR136C | TIS11 | NP_013237 | RNA binding | mRNA-binding protein expressed during iron starvation; binds to a sequence element in the 3′-untranslated regions of specific mRNAs to mediate their degradation; involved in iron homeostasis | zinc finger protein 36, C3H type, homolog | NP_003398.1 | NM_003407.2 |

TABLE 2-continued

| Strength | Type | Systematic Name | Gene Name | Yeast Amino Acid Acc No | Function | Description | Human Homolog | Human Amino Acid Acc No | Human Nucleic Acid Acc No |
|---|---|---|---|---|---|---|---|---|---|
| −2 | enhancer | YGL173C | KEM1 | NP_011342 | RNA binding | Evolutionarily-conserved 5'-3' exonuclease component of cytoplasmic processing (P) bodies involved in mRNA decay; plays a role in microtubule-mediated processes, filamentous growth, ribosomal RNA maturation, and telomere maintenance | 5'-3' exoribonuclease 1 isoform a | NP_061874.3 | NM_019001.3 |
| −2 | enhancer | YGR178C | PBP1 | NP_011694 | RNA binding | Protein interacting with poly(A)-binding protein Pab1p; likely involved in controlling the extent of mRNA polyadenylation; forms a complex with Mkt1p that may regulate HO translation; interacts with Lsm12p in a copurification assay | ataxin 2 | NP_002964.3 | NM_002973.3 |
| −2 | enhancer | YDR335W | MSN5 | NP_010622 | RNA binding | Karyopherin involved in nuclear import and export; shown to be responsible for nuclear import of replication protein A and for export of several proteins including Swi6p, Far1p, and Pho4p; cargo dissociation involves binding to RanGTP | exportin 5 | NP_065801.1 | NM_020750.1 |
| −2 | enhancer | YCL037C | SRO9 | NP_009893 | RNA binding | Cytoplasmic RNA-binding protein that associates with translating ribosomes; involved in heme regulation of Hap1p as a component of the HMC complex, also involved in the organization of actin filaments; contains a La motif | La ribonucleoprotein domain family member 2 | NP_835144 | NM_178043.1 |
| −2 | enhancer | YDR515W | SLF1 | NP_010803 | RNA binding | RNA binding protein that associates with polysomes; proposed to be involved in regulating mRNA translation; involved in the copper-dependent mineralization of copper sulfide complexes on cell surface in cells cultured in copper salts | La ribonucleoprotein domain family member 1; KIAA0731 protein | BAA34451 | AB018274 |
| −2 | enhancer | YOL123W | HRP1 | NP_014518 | RNA binding | Subunit of cleavage factor I, a five-subunit complex required for the cleavage and polyadenylation of pre-mRNA 3' ends; RRM-containing heteronuclear RNA binding protein and hnRNPA/B family member that binds to poly (A) signal sequences | musashi 1; musashi 2 isoform b | NP_002433.1 | NM_002442.2 |
| −1 | enhancer | YBR233W | PBP2 | NP_009792 | RNA binding | RNA binding protein with similarity to mammalian heterogeneous nuclear RNP K protein, involved in the regulation of telomere position effect and telomere length | poly(rC) binding protein 1,2,3,4 | NP_006187.2 | NM_006196.3 |
| 3 | suppressor | YBR112C | CYC8 | NP_009670 | transcription | General transcriptional co-repressor, acts together with Tup1p; also acts as part of a transcriptional co-activator complex that recruits the SWI/SNF and SAGA complexes to promoters | none | none | none |
| 3 | suppressor | YOR380W | RDR1 | NP_015025 | transcription | Transcriptional repressor involved in the control of multidrug resistance; negatively regulates expression of the PDR5 gene; member of the Gal4p family of zinc cluster proteins | none | none | none |
| −2 | enhancer | YOR315W | SFG1 | NP_014960 | transcription | Nuclear protein, putative transcription factor required for growth of superficial pseudohyphae (which do not invade the agar substrate) but not for invasive pseudohyphal growth; may act together with Phd1p; potential Cdc28p substrate | none | none | none |
| 2 | suppressor | YBR157C | ICS2 | NP_009715 | unknown | Protein of unknown function; null mutation does not confer any obvious defects in growth, spore germination, viability, or carbohydrate utilization | mucin 17 | NP_001035194.1 | NM_001040105.1 |
| −2 | enhancer | YOR066W | MSA1 | NP_014709 | unknown | Protein of unknown function; potential Cdc28p substrate | none | none | none |
| −2 | enhancer | YHR131C | YHR131C | NP_011999 | unknown | Putative protein of unknown function; green fluorescent protein (GFP)- fusion protein localizes to the cytoplasm | | | |
| 2 | suppressor | YDL239C | ADY3 | NP_010042 | | Protein required for spore wall formation, thought to mediate assembly of a Don1p-containing structure at the leading edge of the prospore membrane via interaction with spindle pole body components; potentially phosphorylated by Cdc28p | centromere protein E | NP_001804.2 | NM_001813.2 |

TABLE 2-continued

| Strength | Type | Systematic Name | Gene Name | Yeast Amino Acid Acc No | Function | Description | Human Homolog | Human Amino Acid Acc No | Human Nucleic Acid Acc No |
|---|---|---|---|---|---|---|---|---|---|
| 1 | suppressor | YDR369C | XRS2 | NP_010657 | | Protein required for DNA repair; component of the Mre11 complex, which is involved in double strand breaks, meiotic recombination, telomere maintenance, and checkpoint signaling | none | none | none |
| 2 | suppressor | YKL127W | PGM1 | NP_012795 | | Phosphoglucomutase, minor isoform; catalyzes the conversion from glucose-1-phosphate to glucose-6-phosphate, which is a key step in hexose metabolism | PGM1 protein | NP_002624.2 | NM_002633.2 |
| -2 | enhancer | YNR034W | SOL1 | NP_014432 | | Protein with a possible role in tRNA export; shows similarity to 6-phosphogluconolactonase non-catalytic domains but does not exhibit this enzymatic activity; homologous to Sol2p, Sol3p, and Sol4p | 6-phosphogluconolactonase | NP_036220.1 | NM_012088.2 |
| -2 | enhancer | YJL194W | CDC6 | NP_012341 | | Essential ATP-binding protein required for DNA replication, component of the pre-replicative complex (pre-RC) which requires ORC to associate with chromatin and is in turn required for Mcm2-7p DNA association; homologous to S. pombe Cdc18p | cell division cycle 6 protein | NP_001245.1 | NM_001254.3 |
| -3 | enhancer | YDR379W | RGA2 | NP_010667 | | GTPase-activating protein for the polarity-establishment protein Cdc42p; implicated in control of septin organization, pheromone response, and haploid invasive growth | ARHGAP15 | NP_060930.3 | NM_018460.3 |
| -2 | enhancer | YOR008C | SLG1 | NP_014650 | | Sensor-transducer of the stress-activated PKC1-MPK1 kinase pathway involved in maintenance of cell wall integrity; involved in organization of the actin cytoskeleton; secretory pathway Wsc1p is required for the arrest of secretion response | none | none | none |
| -3 | enhancer | YLR371W | ROM2 | NP_013475 | | GDP/GTP exchange protein (GEP) for Rho1p and Rho2p; mutations are synthetically lethal with mutations in rom1, which also encodes a GEP | neuroepithelial cell transforming gene 1 | NP_001040625.1 | NM_001047160.1 |
| -3 | enhancer | YHR158C | KEL1 | NP_012028 | | Protein required for proper cell fusion and cell morphology; functions in a complex with Kel2p to negatively regulate mitotic exit, interacts with Tem1p and Lte1p; localizes to regions of polarized growth; potential Cdc28p substrate | Rab9 effector protein with ketch motifs | NP_005824.2 | NM_005833.2 |
| -2 | enhancer | YER093C | TSC11 | NP_011018 | | Subunit of TORC2 (Tor2p-Lst8p-Avo1-Avo2-Tsc11p-Bit61p), a membrane associated complex that regulates actin cytoskeletal dynamics during polarized growth and cell wall integrity; involved in sphingolipid metabolism; contains a RasGEFN domain | rapamycin-insensitive companion of mTOR (RICTOR) | NP_689969.2 | NM_152756.3 |
| -3 | enhancer | YPL265W | DIP5 | NP_015058 | | Dicarboxylic amino acid permease, mediates high-affinity and high-capacity transport of L-glutamate and L-aspartate; also a transporter for Gln, Asn, Ser, Ala, and Gly | solute carrier family 7 | NP_001070253.1 | NM_001076785.1 |
| -2 | enhancer | YGL023C | PIB2 | NP_011492 | | Protein binding phosphatidylinositol 3-phosphate, involved in telomere-proximal repression of gene expression; similar to Fab1 and Vps27 | WD repeat and FYVE domain containing 3 | NP_055806.2 | NM_014991.4 |
| -2 | enhancer | YDR277C | MTH1 | NP_010563 | | Negative regulator of the glucose-sensing signal transduction pathway, required for repression of transcription by Rgt1p; interacts with Rgt1p and the Snf3p and Rgt2p glucose sensors; phosphorylated by Yck1p, triggering Mth1p degradation | none | none | none |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of inhibiting TDP-43 mediated cellular toxicity, the method comprising contacting a cell comprising a genetic construct for expressing a toxicity inducing amount of a C-terminal variant of TDP-43 consisting of amino acids 188 to 414 of SEQ ID NO: 1, with an effective amount of an agent that inhibits expression or activity of at least one gene selected from the group consisting of DBR1, PCL6, SAK1, YCK2, MEC1, UBP7, RGA2, KEL1, DIP5, ROM2, VHS1, YHR131C, SLF1, HRP1, PBP1, KEM1, MSN5, SRO9, SFG1, MSA1, PIB2, SLG1, MTH1, CDC6, TSC11, SOL1, KIN3, PBP2, SET3, CCE1, SIW14, YDR067C, DOM34, MGD1, RPL16, and human homologs thereof, or an agent that increases expression or activity of at least one gene selected from the group consisting of FMP48, VTS1, XRS2, HSP104, TIS11, BFR1, ICS2, YKL171W, PGM1, ADY3, RIM15, CYC8, RDR1, TIF4631, MRPL39, FLD1, MSN2, PBL16B, NHX1 and human homologs thereof, wherein when said gene is to be inhibited said agent is an antisense, ribozyme or siRNA complementary to mRNA transcribed from said gene such that it binds said mRNA under physiological conditions, and inhibits its translation and wherein when said expression of said gene is to be increased, a vector encoding a polypeptide encoded by said gene is introduced into said cell.

2. The method of claim 1, wherein said gene is DBR1, and said agent is an siRNA comprising a guide strand complementary to DBR1 mRNA which specifically inhibits expression of DBR1.

3. A method for identifying agents which inhibit TDP-43 mediated cellular toxicity, comprising:
 a) providing a cell which comprises a genetic construct for expressing a C-terminal TDP-43 variant consisting of amino acids 188-414 of SEQ ID NO: 1, said expression being associated with increased protein aggregation and cellular toxicity as compared to cells which lack said variant;
 b) contacting said cell with an effective amount of an agent which inhibits expression or activity of at least one gene selected from the group consisting of
  i) PCL6, SAK1, YCK2, MEC1, UBP7, RGA2, KEL1, DIP5, ROM2, VHS1, YHR131C, SLF1, HRP1, PBP1, KEM1, MSN5, SRO9, SFG1, MSA1, PIB2, SLG1, MTH1, CDC6, TSC11, SOL1, KIN3, PBP2, SET3, DBR1, CCE1, SIW14, YDR067C, DOM34, MGD1, RPL16, and human homologs thereof
  ii) an agent which increases expression or activity of at least one gene selected from the group consisting of FMP48, VTS1, XRS2, HSP104, TIS11, BFR1, ICS2, YKL171W, PGM1, ADY3, RIM15, CYC8, RDR1, TIF4631, MRPL39, FLD1, MSN2, PBL16B, NHX1 and human homologs thereof; and
 c) measuring cellular toxicity in the presence of said agent relative to a non-treated control, wherein a decrease in cellular toxicity identifies an agent which reduces TDP-43 mediated cellular toxicity, wherein when said gene is to be inhibited said agent is an antisense, ribozyme or siRNA complementary to mRNA transcribed from said gene such that it binds said mRNA under physiological conditions, and inhibits its translation and wherein when said expression of said gene is to be increased, a vector encoding a polypeptide encoded by said gene is introduced into said cell.

4. The method of claim 3, comprising assessing the effects of said agent on TDP-43 mediated protein aggregation.

5. A transgenic yeast cell comprising,
 i) a genetic construct which, upon expression, produces a C terminal variant TDP-43 protein consisting of amino acids 188 to 414 of SEQ ID NO 1, said yeast cell further comprising
 ii) a nucleic acid construct encoding a TDP-43 activity modifier, said modifier altering TDP-43 toxicity when over expressed, said modifier being selected from the group of modifiers consisting of DBR1, PCL6, SAK1, YCK2, MEC1, UBP7, RGA2, KEL1, DIP5, ROM2, VHS1, YHR131C, SLF1, HRP1, PBP1, KEM1, MSN5, SRO9, SFG1, MSA1, PIB2, SLG1, MTH1, CDC6, TSC11, SOL1, KIN3, PBP2, SET3, CCE1, SIW14, YDR067C, DOM34, MGD1, RPL16, FMP48, VTS1, XRS2, HSP104, TIS11, BFR1, ICS2, YKL171W, PGM1, ADY3, RIM15, CYC8, RDR1, TIF4631, MRPL39, FLD1, MSN2, PBL16B, and NHX1, wherein said nucleic acid construct is heterologous to said yeast cell.

6. The yeast cell of claim 5, wherein over-expression of said modifier reduces TDP-43 cytotoxicity.

7. The yeast cell of claim 5, wherein over-expression of said modifier enhances TDP-43 mediated cytotoxicity.

8. The yeast cell of claim 5, wherein at least one of said constructs comprises an inducible promoter.

9. The method of claim 1, wherein said agent is an antisense, ribozyme or siRNA complementary to DBR1 mRNA such that it binds said DBR1 mRNA under physiological conditions, and inhibits its translation.

* * * * *

```
                            SEQUENCE LISTING

<160> NUMBER OF SEQ ID NOS: 2

<210> SEQ ID NO 1
<211> LENGTH: 414
<212> TYPE: PRT
<213> ORGANISM: Human

<400> SEQUENCE: 1

Met Ser Glu Tyr Ile Arg Val Thr Glu Asp Glu Asn Asp Glu Pro Ile
 1               5                  10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
                35                  40                  45

Gln Cys Met Arg Gly Val Arg Leu Val Glu Gly Ile Leu His Ala Pro
        50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
                100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
                180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
        210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
        290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
```

```
                    340                 345                 350
Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
        370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 2
<211> LENGTH: 4236
<212> TYPE: DNA
<213> ORGANISM: Human

<400> SEQUENCE: 2
```

| | | | | | |
|---|---|---|---|---|---|
| ggtgggcggg | gggaggaggc | ggccctagcg | ccattttgtg | ggagcgaagc | ggtggctggg | 60 |
| ctgcgcttgg | gtccgtcgct | gcttcggtgt | ccctgtcggg | cttcccagca | gcggcctagc | 120 |
| gggaaaagta | aaagatgtct | gaatatattc | gggtaaccga | agatgagaac | gatgagccca | 180 |
| ttgaaatacc | atcggaagac | gatgggacgg | tgctgctctc | cacggttaca | gcccagtttc | 240 |
| caggggcgtg | tgggcttcgc | tacaggaatc | cagtgtctca | gtgtatgaga | ggtgtccggc | 300 |
| tggtagaagg | aattctgcat | gccccagatg | ctggctgggg | aaatctggtg | tatgttgtca | 360 |
| actatccaaa | agataacaaa | agaaaaatgg | atgagacaga | tgcttcatca | gcagtgaaag | 420 |
| tgaaaagagc | agtccagaaa | acatccgatt | taatagtgtt | gggtctccca | tggaaaacaa | 480 |
| ccgaacagga | cctgaaagag | tattttagta | cctttggaga | agttcttatg | gtgcaggtca | 540 |
| agaaagatct | taagactggt | cattcaaagg | ggtttggctt | tgttcgtttt | acggaatatg | 600 |
| aaacacaagt | gaaagtaatg | tcacagcgac | atatgataga | tggacgatgg | tgtgactgca | 660 |
| aacttcctaa | ttctaagcaa | agccaagatg | agcctttgag | aagcagaaaa | gtgtttgtgg | 720 |
| ggcgctgtac | agaggacatg | actgaggatg | agctgcggga | gttcttctct | cagtacgggg | 780 |
| atgtgatgga | tgtcttcatc | cccaagccat | tcagggcctt | tgccttttgtt | acatttgcag | 840 |
| atgatcagat | tgcgcagtct | cttttgtggag | aggacttgat | cattaaagga | atcagcgttc | 900 |
| atatatccaa | tgccgaacct | aagcacaata | gcaatagaca | gttagaaaga | agtggaagat | 960 |
| ttggtggtaa | tccaggtggc | tttgggaatc | agggtggatt | tggtaatagc | agaggggtg | 1020 |
| gagctggttt | gggaaacaat | caaggtagta | atatgggtgg | tgggatgaac | tttggtgcgt | 1080 |
| tcagcattaa | tccagccatg | atggctgccg | cccaggcagc | actacagagc | agttggggta | 1140 |
| tgatgggcat | gttagccagc | cagcagaacc | agtcaggccc | atcgggtaat | aaccaaaacc | 1200 |
| aaggcaacat | gcagagggag | ccaaaccagg | ccttcggttc | tggaaataac | tcttatagtg | 1260 |
| gctctaattc | tggtgcagca | attggttggg | gatcagcatc | caatgcaggg | tcgggcagtg | 1320 |
| gttttaatgg | aggctttggc | tcaagcatgg | attctaagtc | ttctggctgg | ggaatgtaga | 1380 |
| cagtggggtt | gtggttggtt | ggtatagaat | ggtgggaatt | caaattttc | taaactcatg | 1440 |
| gtaagtatat | tgtaaaatac | atatgtacta | agaattttca | aaattggttt | gttcagtgtg | 1500 |
| gagtatattc | agcagtattt | ttgacatttt | tctttagaaa | aaggaagagc | taaggaatt | 1560 |
| ttataagttt | tgttacatga | aaggttgaaa | tattgagtgg | ttgaaagtga | actgctgttt | 1620 |
| gcctgattgg | taaaccaaca | cactacaatt | gatatcaaaa | ggtttctcct | gtaatatttt | 1680 |
| atccctggac | ttgtcaagtg | aattctttgc | atgttcaaaa | cggaaaccat | tgattagaac | 1740 |

```
tacattcttt accccttgtt ttaatttgaa ccccaccata tggatttttt tccttaagaa    1800
aatctccttt taggagatca tggtgtcaca gtgtttggtt cttttgtttt gttttttaac    1860
acttgtctcc cctcatacac aaaagtacaa tatgaagcct tcatttaatc tctgcagttc    1920
atctcatttc aaatgtttat ggaagaagca cttcattgaa agtagtgctg taaatattct    1980
gccataggaa tactgtctac atgctttctc attcaagaat tcgtcatcac gcatcacagg    2040
ccgcgtcttt gacggtgggt gtcccatttt tatccgctac tctttatttc atggagtcgt    2100
atcaacgcta tgaacgcaag gctgtgatat ggaaccagaa ggctgtctga acttttgaaa    2160
ccttgtgtgg gattgatggt ggtgccgagg catgaaaggc tagtatgagc gagaaaagga    2220
gagagcgcgt gcagagactt ggtggtgcat aatggatatt ttttaacttg gcgagatgtg    2280
tctctcaatc ctgtggcttt ggtgagagag tgtgcagaga gcaatgatag caaataatgt    2340
acgaatgttt tttgcattca aaggacatcc acatctgttg gaagacttt aagtgagttt     2400 ttgttcttag ataacccaca ttagatgaat gtgttaagtg aaatgatact tgtactcccc    2460
ctaccccttt gtcaactgct gtgaatgctg tatggtgtgt gttctcttct gttactgata    2520
tgtaagtgtg gcaatgtgaa ctgaagctga tgggctgaga acatggactg agcttgtggt    2580
gtgctttgca ggaggacttg aagcagagtt caccagtgag ctcaggtgtc tcaaagaagg    2640
gtggaagttc taatgtctgt tagctaccca taagaatgct gtttgctgca gttctgtgtc    2700
ctgtgcttgg atgctttta taagagttgt cattgttgga aattcttaaa taaaactgat     2760
ttaaataata tgtgtctttg ttttgcagcc ctgaatgcaa agaattcata gcagttaatt    2820 ccccttttt gacccttttg agatggaact ttcataaagt ttcttggcag tagtttattt     2880
tgcttcaaat aaacttattt gaaaagttgt ctcaagtcaa atggattcat cacctgtcat    2940
gcattgacac ctgatacca gacttaattg gtatttgttc ttgcattggc caaagtgaaa     3000 atttttttt tctttttgaa atctagtttt gaataagtct gggtgaccgc acctaaaatg     3060
gtaagcagta ccctccggct ttttcttagt gcctctgtgc atttgggtga tgttctattt    3120
acatggcctg tgtaaatctc cattgggaag tcatgccttc taaaaagatt cttatttggg    3180
ggagtgggca aaatgttgat tatttctaa tgctttgtag caaagcatat caattgaaaa     3240
gggaatatca gcaccttcct agtttgggat ttgaaaagtg gaattaattg cagtagggat    3300
aaagtagaag aaaccacaaa ttatcttgtg cctgaaatcc attaagaggc ctgatagctt    3360
taagaattag ggtgggttgt ctgtctggaa gtgttaagtg aatgggctt tgtcctccag     3420 gaggtggggg aatgtggtaa cattgaatac agttgaataa aatcgcttac aaaactcaca    3480
ctctcacaat gcattgttaa gtatgtaaaa gcaataacat tgattctctg ttgtactttt    3540
ttgtaactaa ttctgtgaga gttgagctca ttttctagtt ggaagaatgt gatatttgtt    3600
gtgttggtag tttacctaat gcccttacct aattagatta tgataaatag gtttgtcatt    3660
ttgcaagtta cataaacatt tatcaatgaa gtcatccttt agacttgtaa tcgccacatt    3720
gtttcattat tcagtttcct ctgtaaaggg atcttgagtt gttttaattt ttttttttctg   3780 catctgaatc tgcatgattt ccaaaccctg taccatctga attttgcatt ttagcacttg    3840
cactattact cagcagcagt aacatggtaa cacttaaaat ggtactcggg gacctccaaa    3900
gactaaactg acaagccttc aaggagccca ggggtaagtt aacttgtcaa cggcatggtt    3960
taatcccttc tttacacttg tgtaaatttc agttactggt catagaaggc tttcaatgtt    4020
gagtggcctt ttattaacat gtttatggta ctgcatagat acgggtattt attttaccct    4080
```

```
aagaagattt tgaagtttaa aagtacttaa actatttggc aaagatttgt ttttaaaaat    4140
ctatttggtc aatctaaatg cattcattct aaaaaatttt ttgaaccaga taaataaaat    4200 tttttttga caccacaaaa aaaaaaaaaa aaaaaa                               4236
```